(12) United States Patent
Furr et al.

(10) Patent No.: US 10,410,187 B2
(45) Date of Patent: Sep. 10, 2019

(54) MANAGING INSTALLMENT PAYMENTS IN A HEALTHCARE SYSTEM

(71) Applicant: PatientPay, Inc., Durham, NC (US)

(72) Inventors: Thomas Furr, Chapel Hill, NC (US); Anil Kamath, Cary, NC (US)

(73) Assignee: PatientPay, Inc., Durham, NC (US)

( * ) Notice: Subject to any disclaimer, the term of this patent is extended or adjusted under 35 U.S.C. 154(b) by 566 days.

(21) Appl. No.: 14/491,060

(22) Filed: Sep. 19, 2014

(65) Prior Publication Data

US 2015/0006198 A1 Jan. 1, 2015

Related U.S. Application Data

(60) Provisional application No. 61/882,318, filed on Sep. 25, 2013.

(51) Int. Cl.
*G06Q 20/10* (2012.01)
*G06Q 50/22* (2018.01)
(Continued)

(52) U.S. Cl.
CPC ......... *G06Q 20/102* (2013.01); *G06F 19/328* (2013.01); *G06Q 20/227* (2013.01); *G06Q 30/04* (2013.01); *G06Q 50/22* (2013.01)

(58) Field of Classification Search
CPC . G06Q 20/382; G06Q 30/0283; G06Q 20/102
(Continued)

(56) References Cited

U.S. PATENT DOCUMENTS

| 6,879,959 B1 | 4/2005 | Chapman et al. |
| 7,493,266 B2 | 2/2009 | Gupta |

(Continued)

FOREIGN PATENT DOCUMENTS

| JP | 2005141398 | 6/2005 |
| WO | 91/15817 | 10/1991 |

OTHER PUBLICATIONS

Bingham, "Internet-Based Eligibility Verification Lowers Costs, Improves Payment Timeliness," *Healthcare Financial Management*, Feb. 2001, v. 55, n 2, p. 47.
(Continued)

*Primary Examiner* — Reginald R Reyes
(74) *Attorney, Agent, or Firm* — DLA Piper LLP (US)

(57) ABSTRACT

A data management system for managing services rendered within a network of one or more medical service entities and one or more insurance entities includes a provider interface, a payment interface, and a processing engine. The provider interface receives information about one or more medical services in a first format. The processing engine generates an invoice based on the information about the one or more medical services and determines that the invoice is to be paid in a plurality of installments. The payment interface receives each of the plurality of installments from one or more payment services. The provider interface further generates, in a second format, a transaction for each of the plurality of installments and sends said transactions to the one or more medical service entities. The provider interface then transmits information indicating completion of the installments to the one or more medical service entities in the second format.

14 Claims, 59 Drawing Sheets

(51) Int. Cl.
*G06F 19/00* (2018.01)
*G06Q 20/22* (2012.01)
*G06Q 30/04* (2012.01)

(58) Field of Classification Search
USPC .......................................................... 705/2–4
See application file for complete search history.

(56) References Cited

U.S. PATENT DOCUMENTS

| | | | |
|---|---|---|---|
| 7,805,322 B2 | 4/2010 | Flam et al. | |
| 7,925,518 B2 | 4/2011 | Lee et al. | |
| 8,050,938 B1 | 11/2011 | Green, Jr. et al. | |
| 8,155,983 B2 | 4/2012 | Coyne | |
| 8,204,764 B2 | 6/2012 | Coyne | |
| 8,214,233 B2 | 7/2012 | Coyne | |
| 2003/0120592 A1* | 6/2003 | Ng | G06Q 20/04 705/39 |
| 2003/0149594 A1 | 8/2003 | Beazley et al. | |
| 2003/0200118 A1 | 10/2003 | Lee et al. | |
| 2004/0117215 A1 | 6/2004 | Marchosky | |
| 2005/0010438 A1* | 1/2005 | York | G06F 19/328 705/2 |
| 2005/0033609 A1 | 2/2005 | Yang | |
| 2006/0047539 A1 | 3/2006 | Huang | |
| 2006/0143052 A1 | 6/2006 | Fotsch et al. | |
| 2006/0149603 A1 | 7/2006 | Patterson et al. | |
| 2007/0033070 A1 | 2/2007 | Beck et al. | |
| 2007/0033137 A1 | 2/2007 | Provost et al. | |
| 2007/0203750 A1 | 8/2007 | Volcheck | |
| 2007/0208640 A1* | 9/2007 | Banasiak | G06Q 10/04 705/35 |
| 2007/0282637 A1 | 12/2007 | Smith | |
| 2008/0010096 A1 | 1/2008 | Patterson et al. | |
| 2008/0033750 A1 | 2/2008 | Burriss et al. | |
| 2009/0083069 A1 | 3/2009 | Tierney et al. | |
| 2009/0177488 A1 | 7/2009 | Unland et al. | |
| 2009/0313076 A1 | 12/2009 | Schoenberg | |
| 2010/0138243 A1 | 6/2010 | Carroll | |
| 2010/0293065 A1* | 11/2010 | Brody | G06Q 20/16 705/26.1 |
| 2011/0071860 A1* | 3/2011 | Fontenot | G06Q 10/10 705/4 |
| 2013/0129058 A1* | 5/2013 | Kelly | H04M 1/64 379/88.01 |
| 2014/0279685 A1* | 9/2014 | Voutsas | G06Q 40/06 705/36 R |

OTHER PUBLICATIONS

Rouse et al., "The Health Insurance Portability and Accountability Act and its Impact on the Health Care Industry," [Online], 2003, http://business.troy.edu Downloads/Publications/SIRHRC2003/2003SIRHRC/HIPAA.pdf (accessed Sep. 20, 2011).
"Supporting HIPAA Compliance and Streamlining Workflow: HDX Forms Agree with IDX to provide All-Payer Solution," *Business Wire* [Online], 2001.
U.S. Appl. No. 60/974,329, Tierney et al., Sep. 21, 2007.
DotMed News, "Zepherella Introduces 'No Surprise' Healthcare Pricing Solution," Jul. 8, 2009.
Woodside, Joseph, "EDI and ERP; A Real-Time Framework for HealthCare Data Exchange," *J Med Syst* 2008 31:178-184.
Emdeon Claims Management, Web Pages from Jul. 2010.
Employers Direct Health Inc., "Tradelink EDI Corporate Edition," 2006.
Heartland Payment Systems, "Heartland Payment Systems Introduces ConfirmPay," Oct. 12, 2009.
Administrative Services, Inc., "HIPAA Health Care Claim: Professional Transaction Companion Guide," Oct. 2002.
Kazzaz, Danie, "Interactive Adjudication," Aug. 30, 2004.
Capps, Milt, "Healthtech: Zepherella's Tennessee Roll-Out Set for Fall," Jul. 13, 2009.
Emdeon, "Emdeon Payer Solutions," 2010.
NueMD web pages from Oct. 2009.
Medicalbillingsoftware.com, "Medisoft," web pages from Sep. 1999.
PRWeb, "Zepherella Enhances No Surprise Healthcare Pricing Solutions for Physicians with iPhone Application," Jul. 31, 2009.
HPS web pages from Mar. 2008.
PRWeb, "Zepherella Introduces 'No Surprise' Healthcare Pricing Solutions for Physicians with Patient Centered Practices," Jul. 9, 2009.
VestaCare, web pages from May, 2006.
Capital BlueCross "HIPAA ANSI 270/271 Version 4010A1—User Guise," Feb. 1, 2007.

* cited by examiner

Figure 3

| Patient Information | | | |
|---|---|---|---|
| Personal Info | | | |
| Account No | 71234 | Provider | Dr A Provider |
| Last Name | Smith | Date of Birth | 01/01/2000 |
| First Name | John | Sex | Male |
| Address Line 1 | 123 Main Street | Marital Status | Married |
| Address Line 2 | | Social Security | 555-55-5555 |
| City | Springfield | Employer Name | |
| State | NC  Zip  27777 | | |
| Home Phone | (919) 555 1234 | Cell Phone | |
| Work Phone | | | |

Insurances

Add   Update   Remove

| Name | State | Subscriber No | Rel | Insured | Group No |
|---|---|---|---|---|---|
| | | | | | |

OK   Cancel

Figure 4

| | Id | Name | Address Line 1 | City | State | Zip |
|---|---|---|---|---|---|---|
| ☐ | 123 | Academic Insura | 2222 West Main | Springfield | IL | 62716 |
| ☐ | 432 | Academy Insura | 5321 Sussex St | San Diego | CA | 92101 |
| ☑ | 654 | Acme Insurance | PO Box 6457 | Washington | DC | 20066 |

Insurances

Lookup Insurance    ac

OK    Cancel

Figure 5

Patient - Insurance Detail

Insurance

Acme Insurance
PO Box 6457
Washington
DC 20066
Tel: 800-555-1234
Payor Id: 12345

☑ Primary
☐ Secondary
☐ Tertiary

Source of Payment

CI   Commercial

Coverage Dates

01/01/2009   to

Subscriber

Subscriber No
123-456-678

Insured's Name
John Smith

Group No
678

Patient Relationship to Insured
1   Self - patient is the insured

Group Name
Acme HDHP

[ OK ]   [ Cancel ]

Figure 6

| Patient Information | | | |
|---|---|---|---|

Personal Info

| Account No | 71234 | Provider | Dr A Provider |
|---|---|---|---|
| Last Name | Smith | Date of Birth | 01/01/2000 |
| First Name | John | Sex | Male |
| Address Line 1 | 123 Main Street | Marital Status | Married |
| Address Line 2 | | Social Security | 555-55-5555 |
| City | Springfield | Employer Name | |
| State | NC  Zip  27777 | | |
| Home Phone | (919) 555 1234 | Cell Phone | |
| Work Phone | | | |

Insurances

Add    Update    Remove

| Name | State | Subscriber No | Rel | Insured | Group No |
|---|---|---|---|---|---|
| Acme Insuran | DC | 123-456-789 | 1 | John Smith | 678 |

OK    Cancel

Figure 7

| | Id | Name | Address Line 1 | City | State | Zip |
|---|---|---|---|---|---|---|
| ☐ | 456 | Bell Insurance | 2347 East Main | Chicago | IL | 64567 |
| ☑ | 743 | Beta Insurance | 957 Sussex St | San Francisco | CA | 90210 |
| ☐ | 285 | Bex Healthcare | PO Box 5677 | Washington | DC | 20066 |

Insurances

Lookup Insurance  be

OK   Cancel

Figure 8

Patient - Insurance Detail

Insurance

Beta Insurance
957 Sussex St
San Francisco
CA 90210
Tel: 800-555-2222
Payor Id: 76864

☐ Primary
☑ Secondary
☐ Tertiary

Source of Payment

CI   Commercial

Coverage Dates

01/01/2009   to

Subscriber

Subscriber No
456-789-123

Insured's Name
Jane Smith

Patient Relationship to Insured
2   Spouse

Group No
455

Group Name
Beta Healthy Options

OK     Cancel

Figure 9

| Patient Information | | | |
|---|---|---|---|

Personal Info

| Account No | 71234 | Provider | Dr A Provider |
|---|---|---|---|
| Last Name | Smith | Date of Birth | 01/01/2000 |
| First Name | John | Sex | Male |
| Address Line 1 | 123 Main Street | Marital Status | Married |
| Address Line 2 | | Social Security | 555-55-5555 |
| City | Springfield | Employer Name | |
| State | NC  Zip 27777 | | |
| Home Phone | (919) 555 1234 | Cell Phone | |
| Work Phone | | | |

Insurances

Add  Update  Remove

| Name | State | Subscriber No | Rel | Insured | Group No |
|---|---|---|---|---|---|
| Acme Insuran | DC | 123-456-789 | 1 | John Smith | 678 |
| Beta Insuran | CA | 456-789-123 | 2 | Jane Smith | 455 |

OK  Cancel

Figure 10

| | Id | Name | Address Line 1 | City | State | Zip |
|---|---|---|---|---|---|---|
| ✓ | 789 | Z Payer | PO Box 999 | Chapel Hill | NC | 27515 |

Insurances

Lookup Insurance  z

OK   Cancel

Figure 11

```
Patient - Insurance Detail

┌─Insurance─────────────────────────────────────────────────┐
│                                      Source of Payment    │
│  Z Payer                 ☐ Primary   ─────────────────    │
│  PO Box 999              ☐ Secondary  CI   Commercial     │
│  Chapel Hill                                              │
│  NC 27515                ☑ Tertiary  Coverage Dates       │
│  Tel: 800-555-ZPAY                   ──────────────────   │
│  Payor Id: 23336                      01/01/2009  to      │
└───────────────────────────────────────────────────────────┘

┌─Subscriber────────────────────────────────────────────────┐
│                                                           │
│  Subscriber No                                            │
│  ──────────────                                           │
│  111-222-333                                              │
│                                                           │
│  Insured's Name          Patient Relationship to Insured  │
│   John Smith              1    Self - Patient is the insured │
│                                                           │
│  Group No                Group Name                       │
│                                                           │
└───────────────────────────────────────────────────────────┘

[  OK  ]  [ Cancel ]
```

Figure 12

Patient Information

Personal Info

| | | | |
|---|---|---|---|
| Account No | 71234 | Provider | Dr A Provider |
| Last Name | Smith | Date of Birth | 01/01/2000 |
| First Name | John | Sex | Male |
| Address Line 1 | 123 Main Street | Marital Status | Married |
| Address Line 2 | | Social Security | 555-55-5555 |
| City | Springfield | Employer Name | |
| State | NC  Zip  27777 | | |
| Home Phone | (919) 555 1234 | Cell Phone | |
| Work Phone | | | |

Insurances

[ Add ]  [ Update ]  [ Remove ]

| Name | State | Subscriber No | Rel | Insured | Group No |
|---|---|---|---|---|---|
| Acme Insuran | DC | 123-456-789 | 1 | John Smith | 678 |
| Beta Insuranc | CA | 456-789-123 | 2 | Jane Smith | 455 |
| Z Payer | NC | 111-222-333 | 1 | John Smith | |

[ OK ]  [ Cancel ]

Figure 15

HEADER
    BHT   Beginning of Hierarchical Transaction
    LOOP ID    2000A INFORMATION SOURCE LEVEL
        NM1   Payer Name = "ACME INSURANCE"
    LOOP ID    2000B INFORMATION RECEIVER LEVEL
        NM1   Medical Office Name / ID = "GOOD LIFE MEDICAL CLINIC"
    LOOP ID    2000C SUBSCRIBER LEVEL
        NM1   Subscriber Name / ID = "John Smith"
        N3    Subscriber Address
        N4    Subscriber City/State/Zip Code
        DMG  Subscriber Date of Birth
    LOOP ID    2000D DEPENDENT LEVEL
        NM1   Patient Name / ID = "John Smith"
        TRN   Trace Number
        PRV   Rendering Provider ID
        DMG  Patient Date of Birth
        LOOP ID    2110D DEPENDENT ELIGIBILITY OR BENEFIT INQUIRY
            EQ    Eligibility or Benefit Inquiry, inc:
                    EQ02 Composite Medical Procedure Id
            DTP   Service Date = "4 January 2010"

Figure 16

HEADER
    BHT   Beginning of Hierarchical Transaction
    LOOP ID    2000A INFORMATION SOURCE LEVEL
        NM1   Payer Name = "ACME INSURANCE"
    LOOP ID    2000B INFORMATION RECEIVER LEVEL
        NM1   Medical Office Name / ID = "GOOD LIFE MEDICAL CLINIC"
    LOOP ID    2000C SUBSCRIBER LEVEL
        NM1   Subscriber Name / ID = "John Smith"
        N3    Subscriber Address
        N4    Subscriber City/State/Zip Code
        DMG  Subscriber Date of Birth
    LOOP ID    2000D DEPENDENT LEVEL
        NM1   Patient Name / ID = "John Smith"
        TRN   Trace Number
        DMG  Patient Date of Birth
        LOOP ID    2110D DEPENDENT ELIGIBILITY OR BENEFIT INFORMATION
            EB    Eligibility or Benefit Information, inc:
                    EB01 Eligibility and Benefit Information Code = 1
                    EB07 Amount Pre-Authorized for Service
                    EB13 Composite Medical Procedure Identifier
            DTP   Service Date = "4 January 2010"

Figure 17

HEADER
    BHT   Beginning of Hierarchical Transaction
    LOOP ID    2000A INFORMATION SOURCE LEVEL
        NM1   Payer Name = "Z PAYER"
    LOOP ID    2000B INFORMATION RECEIVER LEVEL
        NM1   Medical Office Name / ID = "GOOD LIFE MEDICAL CLINIC"
    LOOP ID    2000C SUBSCRIBER LEVEL
        NM1   Subscriber Name / ID = "John Smith"
        N3    Subscriber Address
        N4    Subscriber City/State/Zip Code
        DMG  Subscriber Date of Birth
    LOOP ID    2000D DEPENDENT LEVEL
        NM1   Patient Name / ID = "John Smith"
        TRN   Trace Number
        PRV   Rendering Provider ID
        DMG  Patient Date of Birth= "17 September 1983"
        LOOP ID    2110D DEPENDENT ELIGIBILITY OR BENEFIT INQUIRY
            EQ    Eligibility or Benefit Inquiry, inc:
                    EQ02 Composite Medical Procedure Id
            DTP   Service Date = "4 January 2010"

Figure 20

```
HEADER
    BHT   Beginning of Hierarchical Transaction
    LOOP ID    2000A INFORMATION SOURCE LEVEL
        NM1   Payer Name = "Z PAYMENT COMPANY"
    LOOP ID    2000B INFORMATION RECEIVER LEVEL
        NM1   Medical Office Name / ID = "GOOD LIFE MEDICAL CLINIC"
    LOOP ID    2000C SUBSCRIBER LEVEL
        NM1   Subscriber Name / ID = "John Smith"
        N3    Subscriber Address
        N4    Subscriber City/State/Zip Code
        DMG   Subscriber Date of Birth
    LOOP ID    2000D DEPENDENT LEVEL
        NM1   Patient Name / ID = "John Smith"
        TRN   Trace Number
        DMG   Patient Date of Birth
        LOOP ID    2110D DEPENDENT ELIGIBILITY OR BENEFIT INFORMATION
            EB    Eligibility or Benefit Information, inc:
                    EB01 Eligibility and Benefit Information Code = 1
                    EB07 Amount Pre-Authorized for Service
                    EB13 Composite Medical Procedure Identifier
            DTP   Service Date = "4 January 2010"
```

Figure 21

| Claim | | | | |
|---|---|---|---|---|
| Claim No | Claim Date | Service Date | Appointment Facility | |
| 12345 | 08/15/2010 | 08/13/2010 | Good Life Medical Clinic | |

Patient

John Smith
DOB: 01/01/2001
Tel: 919-555-1234
Acct No: 71234

CoPay

Outstanding Balance
$217.53

Provider

Billing — Good Life Medical Clinic
Rendering — Dr A Provider
Referring —

Claim Status — Bill to Primary

Services | Payments | Additional Info

Diagnosis Codes

| | Code | Name |
|---|---|---|
| 1 | V20.2 | Well Child Exam |
| | | |
| | | |

Insurances

| | Name |
|---|---|
| P | Acme Insurance |
| S | Beta Insurance |
| T | Z Payer |

| Code | DOS | M1 | M2 | M3 | I1 | I2 | I3 | U | Billed Amt |
|---|---|---|---|---|---|---|---|---|---|
| 99393 | 08/13/2010 | 25 | | | 1 | | | 1 | $217.53 |
| | | | | | | | | | |
| | | | | | | | | | |

OK    Cancel

Figure 22

| Claim | | | | |
|---|---|---|---|---|
| Claim No | Claim Date | Service Date | Appointment Facility | |
| 12345 | 08/15/2010 | 08/13/2010 | Good Life Medical Clinic | |

Patient

John Smith
DOB: 01/01/2001
Tel: 919-555-1234
Acct No: 71234

CoPay
$20.00

Outstanding Balance
$0.00

Provider

Billing: Good Life Medical Clinic
Rendering: Dr A Provider
Referring:

Claim Status: Paid in Full

Services | Payments | Additional Info

Insurances

|   | Name | State | Subscriber No | Rel | Insured |
|---|---|---|---|---|---|
| P | Acme Insurance | DC | 123-456-678 | 1 | Smith, John |
| S | Beta Insurance | CA | 456-789-123 | 2 | Smith, Jane |
| T | Z Payer | NC | 111-222-333 | 1 | Smith, John |

Payment/Adjustments/Refunds

| Id | From | Date | Allowed | P/R | Paid | Adj |
|---|---|---|---|---|---|---|
| 123 | Acme Insurance | 08/25/2010 | $171.43 | $20.00 | $151.43 | $46.10 |
| 128 | Beta Insurance | 09/02/2010 | $0.00 | $10.00 | $10.00 | $0.00 |
| 156 | Z Payer | 09/06/2010 | $0.00 | $0.00 | $9.00 | $1.00 |

( OK )  ( Cancel )

Figure 26 A

HEADER

BHT
    REF    ANSI ASC X12N 837
    LOOP ID    1000A SUBMITTER NAME
        NM1    Submitter Name
        PER    Submitter EDI Contact Information
    LOOP ID    1000B RECEIVER NAME
        NM1    Receiver Name LOOP ID    2000A BILLING/PAY-TO PROVIDER HIERARCHICAL LEVEL
        HL    Information Source (20)

LOOP ID    2010AA BILLING PROVIDER NAME
        NM1    Billing Provider Name / ID = GOOD LIFE MEDICAL CLINIC
        N3    Billing Provider Address
        N4    Billing Provider City/State/Zip Code
        REF    Billing Provider Tax Id LOOP ID    2000B SUBSCRIBER HIERARCHICAL LEVEL
        HL    Subscriber (22)
        SBR    Subscriber Information (Subscriber is Patient)
        LOOP ID    2010BA SUBSCRIBER NAME
            NM1    Subscriber Name / ID = JOHN SMITH
            N3    Subscriber Address
            N4    Subscriber City/State/Zip Code
        LOOP ID    1010BB PAYER NAME
            NM1    Payer Name / ID = ACME INSURANCE
            N3    Payer Address
            N4    Payer City/State/Zip Code

Figure 26 B

```
LOOP ID     2300 CLAIM INFORMATION
    CLM     Claim Information incs:
                CLM02 Billed Amount for Claim = $217.53
    HI      Health Care Diagnosis Codes
    LOOP ID     2310A REFERRING PROVIDER NAME
        NM1     Referring Provider Name / ID
    LOOP ID     2310B RENDERING PROVIDER NAME
        NM1     Rendering Provider Name / ID
    LOOP ID     2400 SERVICE LINE
        LX      Assigned Number
        SV1     Professional Service Information
        DTP     Service Date
        LOOP ID     2420A RENDERING PROVIDER NAME
            NM1     Rendering Provider Name / ID
        LOOP ID     2420F REFERRING PROVIDER NAME
            NM1     Referring Provider Name / ID
```

Figure 27

```
HEADER
    BPR    Financial Information inc
                BPR02 Total Provider Payment Amt = $151.43
    TRN    Trace Number
    REF    Version Number
    DTM    Production Date
    LOOP ID      1000A PAYER IDENTIFICATION
        N1     Payer Name / ID = ACME INSURANCE
        N3     Payer Address
        N4     Payer City/State/Zip Code
    LOOP ID      1000B PAYEE IDENTIFICATION
        N1     Payee Name / ID = GOOD LIFE MEDICAL CLINIC
        N3     Payee Address
        N4     Payee City/State/Zip Code
        REF    Payee Tax Id
    LOOP ID      2000 HEADER NUMBER
        LX     Assigned Number
        LOOP ID      2100 CLAIM PAYMENT INFORMATION
            CLP    Claim Payment Information, inc:
                        CLP03 Total Claim Charge Amount = $217.53
                        CLP04 Claim Payment Amount = $151.43
                        CLP05 Patient Responsibility Amount = $20.00
            NM1    Patient Name / ID = JOHN SMITH
            NM1    Insured Name / ID = JOHN SMITH
            NM1    Rendering Provider Name / ID
            LOOP ID      2110 SERVICE PAYMENT INFORMATION
                SVC    Service Line Information, inc:
                            SVC01 Composite Medical Procedure Id
                            SVC02 Line Charge Amt = $217.53
                            SVC03 Line Provider Payment Amt = $151.43
                DTM    Service Date
                CAS    Claims Adjustment, inc
                            CAS03 Contractual Obligations = $46.10
                            CAS03 Patient Responsibility = $20.00
```

Figure 28 A

HEADER

```
BHT
REF    ANSI ASC X12N 837
LOOP ID    1000A SUBMITTER NAME
    NM1    Submitter Name
    PER    Submitter EDI Contact Information
LOOP ID    1000B RECEIVER NAME
    NM1    Receiver Name LOOP ID    2000A BILLING/PAY-TO PROVIDER HIERARCHICAL LEVEL
    HL    Information Source (20)

LOOP ID    2010AA BILLING PROVIDER NAME
    NM1    Billing Provider Name / ID = GOOD LIFE MEDICAL CLINIC
    N3    Billing Provider Address
    N4    Billing Provider City/State/Zip Code
    REF    Billing Provider Tax Id LOOP ID    2000B SUBSCRIBER HIERARCHICAL LEVEL
    HL    Subscriber (22)
    SBR    Subscriber Information (Subscriber is Patient)
    LOOP ID    2010BA SUBSCRIBER NAME
        NM1    Subscriber Name / ID = JANE SMITH
        N3    Subscriber Address
        N4    Subscriber City/State/Zip Code
    LOOP ID    1010BB PAYER NAME
        NM1    Payer Name / ID = BETA INSURANCE
        N3    Payer Address
        N4    Payer City/State/Zip Code LOOP ID    2300 CLAIM INFORMATION
        CLM    Claim Information incs:
                CLM02 Billed Amount for Claim = $217.53
        HI    Health Care Diagnosis Codes
        LOOP ID    2310A REFERRING PROVIDER NAME
            NM1    Referring Provider Name / ID
        LOOP ID    2310B RENDERING PROVIDER NAME
            NM1    Rendering Provider Name / ID
        LOOP ID    2320 OTHER SUBSCRIBER INFORMATION
            SBR    Subscriber Information
            AMT    COB Payer Paid Amt = $151.43
```

Figure 28 B

```
        AMT   COB Allowed Amt = $171.43
LOOP ID       2330A OTHER SUBSCRIBER NAME
        NM1   Other Subscriber Name / ID = JOHN SMITH
LOOP ID       2330B OTHER PAYER NAME
        NM1   Other Payer Name / ID = ACME INSURANCE / 12345
LOOP ID       2400 SERVICE LINE
        LX    Assigned Number
        SV1   Professional Service Information
        DTP   Service Date
        LOOP ID    2420A RENDERING PROVIDER NAME
              NM1  Rendering Provider Name / ID
        LOOP ID    2420F REFERRING PROVIDER NAME
              NM1  Referring Provider Name / ID
        LOOP ID    2430 LINE ADJUDICATION INFORMATION
              SVD  Service Line Adjudication inc
                        SVD01 Other Payer ID = 12345
                        SVD02 Service Line Paid Amt = $151.43
              CAS  Line Adjustment inc
                        CAS03 Patient Responsibility = $20.00
              DTP  Date Claim Paid
```

Figure 29

HEADER
    BPR    Financial Information inc
                BPR02 Total Provider Payment Amt = $10.00
    TRN    Trace Number
    REF    Version Number
    DTM    Production Date
    LOOP ID    1000A PAYER IDENTIFICATION
        N1    Payer Name / ID = BETA INSURANCE
        N3    Payer Address
        N4    Payer City/State/Zip Code
    LOOP ID    1000B PAYEE IDENTIFICATION
        N1    Payee Name / ID = GOOD LIFE MEDICAL CLINIC
        N3    Payee Address
        N4    Payee City/State/Zip Code
        REF    Payee Tax Id
    LOOP ID    2000 HEADER NUMBER
        LX    Assigned Number
        LOOP ID    2100 CLAIM PAYMENT INFORMATION
            CLP    Claim Payment Information, inc:
                    CLP03 Total Claim Charge Amount = $217.53
                    CLP04 Claim Payment Amount = $10.00
                    CLP05 Patient Responsibility Amount = $10.00
            NM1    Patient Name / ID = JOHN SMITH
            NM1    Insured Name / ID = JOHN SMITH
            NM1    Rendering Provider Name / ID
            LOOP ID    2110 SERVICE PAYMENT INFORMATION
                SVC    Service Line Information, inc:
                        SVC01 Composite Medical Procedure Id
                        SVC02 Line Charge Amt = $217.53
                        SVC03 Line Provider Payment Amt = $10.00
                DTM    Service Date
                CAS    Claims Adjustment, inc
                        CAS03 Other Payer Adjustments = $207.53
                        CAS03 Patient Responsibility = $10.00

Figure 30 A

HEADER

```
BHT
REF    ANSI ASC X12N 837
LOOP ID    1000A SUBMITTER NAME
    NM1    Submitter Name
    PER    Submitter EDI Contact Information
LOOP ID    1000B RECEIVER NAME
    NM1    Receiver Name LOOP ID    2000A BILLING/PAY-TO PROVIDER HIERARCHICAL LEVEL
    HL    Information Source (20)

LOOP ID    2010AA BILLING PROVIDER NAME
    NM1    Billing Provider Name / ID = GOOD LIFE MEDICAL CLINIC
    N3    Billing Provider Address
    N4    Billing Provider City/State/Zip Code
    REF    Billing Provider Tax Id LOOP ID    2000B SUBSCRIBER HIERARCHICAL LEVEL
    HL    Subscriber (22)
    SBR    Subscriber Information (Subscriber is Patient)
    LOOP ID    2010BA SUBSCRIBER NAME
        NM1    Subscriber Name / ID = JOHN SMITH
        N3    Subscriber Address
        N4    Subscriber City/State/Zip Code
    LOOP ID    1010BB PAYER NAME
        NM1    Payer Name / ID = Z PAYER
        N3    Payer Address = 123 Oak Street
        N4    Payer City/State/Zip Code = Anytown, NC 45678

LOOP ID    2300 CLAIM INFORMATION
            CLM    Claim Information Inc
                   CLM02 Billed Amount for Claim = $217.53
            HI    Health Care Diagnosis Codes
            LOOP ID    2310A REFERRING PROVIDER NAME
                NM1    Referring Provider Name / ID
            LOOP ID    2310B RENDERING PROVIDER NAME
                NM1    Rendering Provider Name / ID
            LOOP ID    2320 OTHER SUBSCRIBER INFORMATION
                SBR    Subscriber Information
                AMT    COB Payer Paid Amt = $151.43
```

Figure 30 B

```
              AMT     COB Allowed Amt = $171.43
         LOOP ID      2330A OTHER SUBSCRIBER NAME
              NM1     Other Subscriber Name / ID = JOHN SMITH
         LOOP ID      2330B OTHER PAYER NAME
              NM1     Other Payer Name / ID = ACME INSURANCE / 12345
         LOOP ID      2320 OTHER SUBSCRIBER INFORMATION
              SBR     Subscriber Information
              AMT     COB Payer Paid Amt = $10.00
         LOOP ID      2330A OTHER SUBSCRIBER NAME
              NM1     Other Subscriber Name / ID = JANE SMITH
         LOOP ID      2330B OTHER PAYER NAME
              NM1     Other Payer Name / ID = BETA INSURANCE / 54321
LOOP ID       2400 SERVICE LINE
              LX      Assigned Number
              SV1     Professional Service Information
              DTP     Service Date
              LOOP ID      2420A RENDERING PROVIDER NAME
                   NM1     Rendering Provider Name / ID
              LOOP ID      2420F REFERRING PROVIDER NAME
                   NM1     Referring Provider Name / ID
              LOOP ID      2430 LINE ADJUDICATION INFORMATION
                   SVD     Service Line Adjudication inc
                                SVD01 Other Payer ID = 12345
                                SVD02 Service Line Paid Amt = $151.43
                   CAS     Line Adjustment inc
                                CAS03 Patient Responsibility = $20.00
                   DTP     Date Claim Paid
              LOOP ID      2430 LINE ADJUDICATION INFORMATION
                   SVD     Service Line Adjudication inc
                                SVD01 Other Payer ID = 54321
                                SVD02 Service Line Paid Amt = $10.00
                   CAS     Line Adjustment inc
                                CAS03 Patient Responsibility = $10.00
                   DTP     Date Claim Paid
```

Figure 31

```
HEADER
    BPR    Financial Information inc
                BPR02 Total Provider Payment Amt = $9.00
    TRN    Trace Number
    REF    Version Number
    DTM    Production Date
    LOOP ID     1000A PAYER IDENTIFICATION
        N1     Payer Name / ID = Z PAYER
        N3     Payer Address
        N4     Payer City/State/Zip Code
    LOOP ID     1000B PAYEE IDENTIFICATION
        N1     Payee Name / ID = GOOD LIFE MEDICAL CLINIC
        N3     Payee Address
        N4     Payee City/State/Zip Code
        REF    Payee Tax Id
    LOOP ID     2000 HEADER NUMBER
        LX     Assigned Number
        LOOP ID      2100 CLAIM PAYMENT INFORMATION
            CLP    Claim Payment Information, inc:
                        CLP03 Total Claim Charge Amount = $217.53
                        CLP04 Claim Payment Amount = $9.00
                        CLP05 Patient Responsibility Amount = $0.00
            NM1    Patient Name / ID = JOHN SMITH
            NM1    Insured Name / ID = JOHN SMITH
            NM1    Rendering Provider Name / ID
            LOOP ID      2110 SERVICE PAYMENT INFORMATION
                SVC    Service Line Information, inc:
                            SVC01 Composite Medical Procedure Id
                            SVC02 Line Charge Amt = $217.53
                            SVC03 Line Provider Payment Amt = $9.00
                DTM    Service Date
                CAS    Claims Adjustment, inc
                            CAS03 Other Payer Adjustments = $207.53
                            CAS05 Collection Fee Adjustment = $1.00
```

Create An Appointment

Create New Account
(Subscriber Id is an email address)

* New account is generated by the system. A complete registration email is sent to the account holder.
** Information from these fields are used to populate these records where possible. Member_Id's are allocated by the payment system

MANAGING INSTALLMENT PAYMENTS IN A HEALTHCARE SYSTEM

TECHNICAL FIELD

This disclosure relates generally to health care systems and, more particularly, to managing installment payments in a health care system to compensate health care providers.

BACKGROUND

The increasing cost of health insurance induces insurers to seek new ways to contain increases in healthcare costs. A primary method to achieve this is through various methods of cost shifting from the insurer to patients. By having patients be responsible for an increasing portion of their healthcare spending, the insurers believe that patients will become smarter consumers of healthcare and help to reduce the overall costs. As a result, the proportion of payments from the patient to the physician, as opposed to from the insurer to the physician, increases.

SUMMARY

A data management system for managing payments for services rendered is provided. The data management system operates within a network of one or more medical service entities that provide medical services and one or more insurance entities that provide insurance. The data management system, medical service entities, and insurance entities communicate with one another via standardized transactions, where a first format is used in transactions from the medical service entities to the data management system and the insurance entities, and where a second format is used in transactions from the data management system and the insurance entities to the medical service entities. The data management system includes a provider interface configured to receive a request transaction related to payment for one or more patient-rendered medical services performed by a first of the one or more medical entities, and to transmit a payment transaction for the one or more patient-rendered medical services. The request transaction is automatically provided to the provider interface based upon the data management system being registered with the first of the one or more medical entities as a payer for a patient. The data management system further includes a processing engine configured to process the received request transaction to identify the patient and an amount due, and to construct the payment transaction. A payment engine is configured to obtain payment authorization and process the amount due. Information related to the payment authorization and processing of the amount due are populated in the payment transaction.

According to another embodiment, a data management system for managing HIPAA transactions for patient care is provided. The data management system operates within a network of one or more medical service entities that provide medical services and one or more insurance entities that provide insurance. The data management system, medical service entities, and insurance entities communicate with one another via standardized HIPAA transactions, where HIPAA 270 transactions are used from the medical service entities to the data management system and the insurance entities, and where HIPAA 271 transactions are used from the data management system and the insurance entities to the medical service entities. The data management system includes a provider interface configured to receive a HIPAA 270 eligibility-benefits transaction containing information related to one or more scheduled medical services for a patient to be performed by a first of the one or more medical entities, and to transmit a HIPAA 271 eligibility-benefits confirmation transaction. The HIPAA 270 eligibility-benefits transaction is automatically provided to the provider interface based upon the data management system being registered with the first of the one or more medical entities as a payer for the patient. The data management system also includes an eligibility-benefits engine configured to (i) determine an eligibility status for the patient based on a valid payment confirmation for covering at least a portion of fees related to the one or more scheduled medical services and data in the HIPAA 270 eligibility-benefits transaction matching data in one of a plurality of registration records, (ii) create an appointment record for the patient, and (iii) create the HIPAA 271 eligibility-benefits confirmation transaction indicating the eligibility status for the patient.

A method is provided for managing HIPAA transactions for patient care. The method includes receiving at a provider interface a HIPAA 270 eligibility-benefits transaction containing information related to one or more scheduled medical services for a patient to be performed by a first of one or more medical entities. An eligibility status for the patient is determined by an eligibility-benefits engine based on a valid payment confirmation for covering at least a portion of fees related to the one or more scheduled medical services and data in the HIPAA 270 eligibility-benefits transaction matching data in one of a plurality of registration records. The method further includes creating, by the eligibility-benefits engine, an appointment record and a HIPAA 271 eligibility-benefits confirmation transaction indicating the eligibility status for the patient. The HIPAA 271 eligibility-benefits confirmation transaction is transmitted from the provider interface. The provider interface subsequently receives a HIPAA 837 payment request transaction related to payment for one or more patient-rendered medical services. The HIPAA 837 payment request transaction is processed at a processing engine to identify the patient and an amount due. Payment authorization and the amount due are processed by a payment engine. The processing engine constructs a HIPAA 835 payment confirmation transaction, where information related to the payment authorization and processing of the amount due are populated in the HIPAA 835 payment confirmation transaction. The HIPAA 835 payment confirmation transaction is then transmitted from the provider interface. The provider interface, the eligibility-benefits engine, the processing engine, and the payment engine together comprise a data management system that operates within a network of the one or more medical service entities that provide medical services and one or more insurance entities that provide insurance. Furthermore, the HIPAA 270 eligibility-benefits transaction and the HIPAA 837 payment request transaction are automatically provided to the provider interface based upon a registration of the data management system with the first of the one or more medical entities as a payer for the patient. The data management system, the one or more medical service entities, and the one or more insurance entities communicate with one another via standardized HIPAA transactions, where HIPAA 270 and HIPAA 837 transactions are used from the one or more medical service entities to the data management system and the one or more insurance entities, and where HIPAA 271 and HIPAA 835 transactions are used from the data management system and the one or more insurance entities to the one or more medical service entities.

In some embodiments, the data management system may accept installment payments. The data management system includes a provider interface in communication with the one or more medical service entities, the provider interface configured to communicate with the one or more medical service entities via the standardized transactions, so that transactions from the one or more medical service entities to the provider interface are in the first format and transactions from the provider interface to the medical service entities are in the second format. The data management system also includes a payment interface embodied in at least one computing device executing computer-readable instructions, said payment interface in communication with one or more payment services and configured to request payment of a designated amount in connection with any charges for the one or more medical services. The data management system also includes a processing engine embodied in at least one computing device executing computer-readable instructions, said processing engine configured to apply any payments from the one or more insurance entities and any payments from the one or more payment services, in connection with any charges for the one or more medical services. The provider interface is configured to receive information about the one or more medical services from the one or more medical service entities in the first format. The processing engine is configured to generate an invoice based on the information about the one or more medical services received by the provider interface and determine that the invoice is to be paid in a plurality of installments. The payment interface is configured to receive each of the plurality of installments from the one or more payment services. The provider interface is configured to generate, in the second format, a transaction for each of the plurality of installments comprising information about the installment and send each of the transactions to the one or more medical service entities. When transactions for each of the plurality of installments have been generated, the provider interface is configured to transmit information indicating completion of the plurality of installments to the one or more medical service entities in the second format.

BRIEF DESCRIPTION OF THE DRAWINGS

The foregoing summary and the following detailed description are better understood when read in conjunction with the appended drawings. Representative examples are shown in the drawings. However, it is understood that the examples are not limited to the specific methods and instrumentalities depicted herein. In the drawings:

FIG. 3 is an image displayed on an output screen.

FIG. 4 is an image displayed on the output screen at a time subsequent to that depicted in FIG. 3.

FIG. 5 is an image displayed on the output screen at a time subsequent to that depicted in FIG. 4.

FIG. 6 is an image displayed on the output screen at a time subsequent to that depicted in FIG. 5.

FIG. 7 is an image displayed on the output screen at a time subsequent to that depicted in FIG. 6.

FIG. 8 is an image displayed on the output screen at a time subsequent to that depicted in FIG. 7.

FIG. 9 is an image displayed on the output screen at a time subsequent to that depicted in FIG. 8.

FIG. 10 is an image displayed on the output screen at a time subsequent to that depicted in FIG. 9.

FIG. 11 is an image displayed on the output screen at a time subsequent to that depicted in FIG. 10.

FIG. 12 is an image displayed on the output screen at a time subsequent to that depicted in FIG. 11.

FIG. 15 is a diagram showing a message in more detail.

FIG. 16 is a diagram showing a message in more detail.

FIG. 17 is a diagram showing a message in more detail.

FIG. 20 is a diagram showing a message in more detail.

FIG. 21 shows an output screen image for entering a claim for payment for medical services rendered.

FIG. 22 shows a report detailing payments received from various payers.

FIGS. 26A and 26B constitute a diagram showing a message in more detail.

FIG. 27 is a diagram showing a message in more detail.

FIGS. 28A and 28B constitute a diagram showing a message in more detail.

FIG. 29 is a diagram showing a message in more detail.

FIGS. 30A and 30B constitute a diagram showing a message in more detail.

FIG. 31 is a diagram showing a message in more detail.

DETAILED DESCRIPTION

Figure 1:
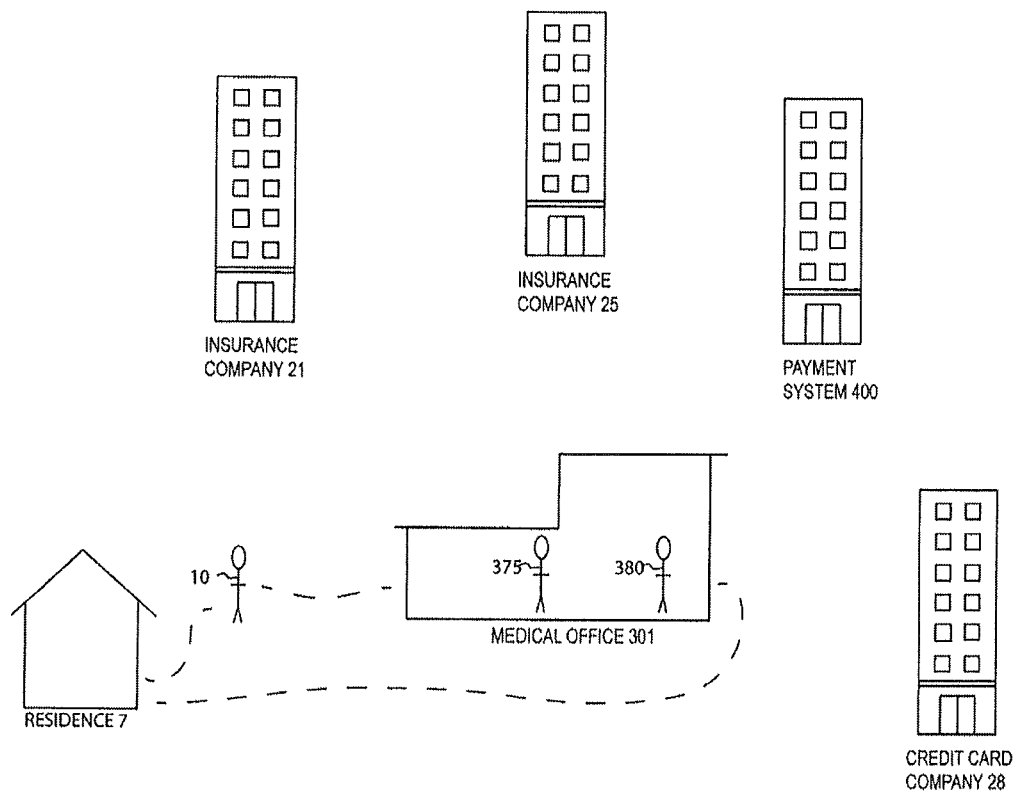
FIG. 1 shows a system 1 in accordance with an embodiment.

FIG. 1 shows system 1. Person 10 has a subscriber relationship with insurance company 21, meaning that person 10 has a contract with insurance company 21, the contract providing that person 10 pay insurance company 21 before medical costs accrue. Insurance company 21 has an obligation to pay for medical costs as they accrue, provided certain conditions are satisfied.

Person 10 has a dependent relationship with insurance company 25, meaning that person 10's spouse has a contract with insurance company 25 in which person 10 is covered as a dependent, the contract providing that person 10's spouse pay insurance company 25 before medical cost accrue. Insurance company 25 has an obligation to pay for medical costs as they accrue, provided certain conditions are satisfied.

Person 10 has a card holder relationship with credit card company 28, meaning that credit card company 28 may pay a cost when the cost accrues and person 10 is then obligated to compensate credit card company and, under certain conditions, pay interest.

Credit card company 28 is a card-issuing bank, an organization that issues credit cards to consumers. Credit card company 28 bills consumers for repayment and bears the risk that an issued card is used fraudulently. Credit card company 28 is a member of an association of card-issuing banks that participate in a network such as Visa, MasterCard, Discover, American Express, etc. The association sets transaction terms for merchants and card-issuing banks.

Figure 2:
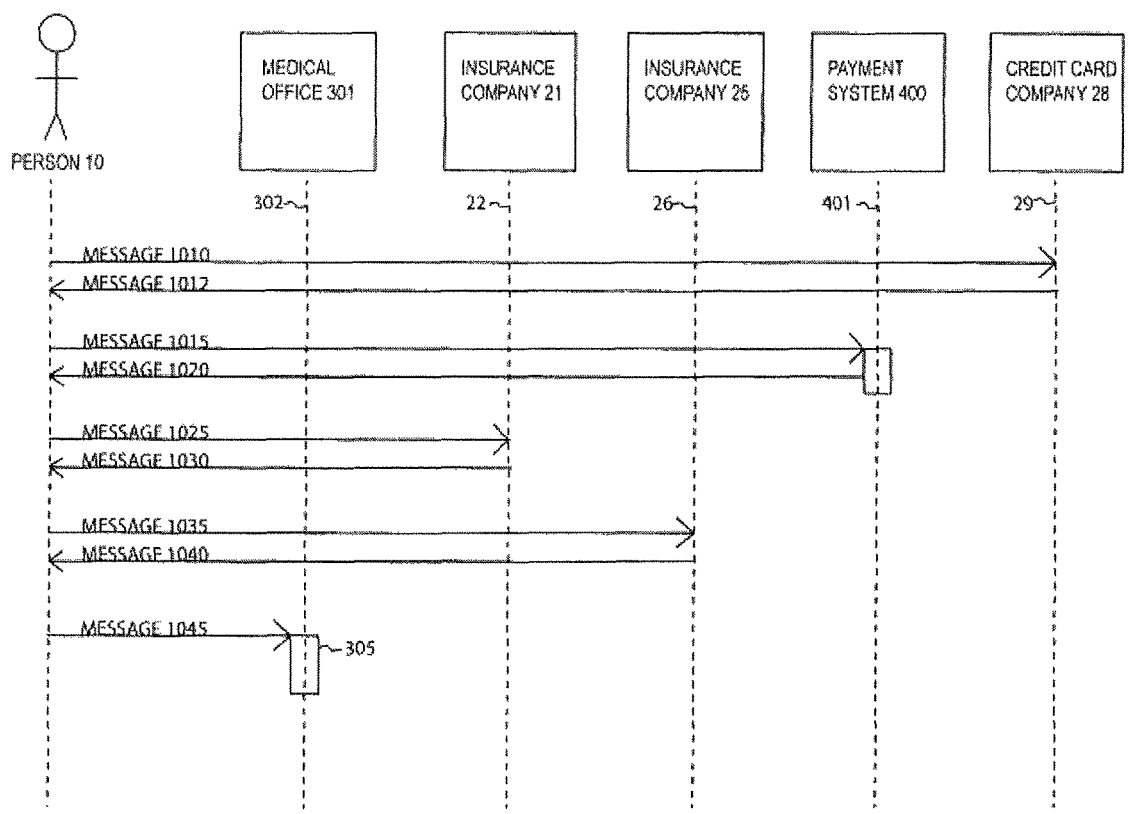
FIG. 2 shows a sequence of messages in system 1.

With reference to FIG. 2, responsive to an appointment request from person 10, staff in medical office 301 invokes a computer-program to send a message to payment system 400 to determine patient eligibility in payment system 400. The message includes a HIPAA 270 transaction, including information regarding the appointment, such as the appointment date, the patient name and ID, the account holder name and ID, and expected, services to be performed.

Responsive to receiving the HIPAA 270 transaction, payment system 400 generates a HIPAA 271 transaction to respond to the HIPAA 270 inquiry, thereby informing medical office 301 regarding whether person 10 is set up in payment system 400 with a valid payment method (i.e. are they eligible based on the information system 400 has at present). If person 10 is already set up in payment system 400 and the payment card account of person 10 is valid, then the payment system 400 will automatically set up an appointment record for person 10 based on the information in the HIPAA 270 inquiry. If person 10 is not already set up in payment system 400 or the payment card account of person 10 is not valid, then payment system 400 will set up an appointment record and send an email to person 10, enabling person 10 to either register or update their payment card prior to the appointment with medical office 301.

In summary, system 400 emulates an insurance company to use HIPAA 270/271 transactions to communicate appointment scheduling information between the payment system 400 and the medical office practice management system without requiring any changes to the legacy code. As such the personnel at medical office 301 do not need to set up appointments directly within payment system 400.

Subsequently, Person 10 visits medical office 301 (i.e., "Good Life Medical Clinic") and receives a medical service, such as an office visit with a blood test or antibiotic injection. Person 10 sees doctor 375. At appointment checkout, person 10 sees office administrator 380. Medical office 301 accordingly generates a charge.

In order to collect payment from payment system 400, medical office 301 sets up payment system 400 as a standard 'payer' in the medical office practice management system (PMS) such that payment system 400 emulates an insurance company. For person 10, medical office 301 sets up payment system 400 as a tertiary payer, or the payer of last resort.

For person 10, medical office 301 sends an ANSI ASC X12N 837 Health Care claims (837) transaction (HIPAA 837 transaction) to person 10's primary insurer, insurance company 21.

In response to receiving the HIPAA 837 transaction from medical office 301, insurance company 21 sends a X12N 835 Health Care Claims Payment Advice transaction (HIPAA 835 transaction) that explains an adjudication ruling based on a contract between medical office 301 and insurance company 21, and a contract between person 10 and insurance company 21 (person 10's eligibility and benefits). The HIPAA 835 transaction provides medical office 301 remittance advice corresponding to the received 837 transaction, along with a detailed breakdown of payment and adjustments to the billed amount. The HIPAA 835 transaction includes amount, payee, payer, and payment method. The HIPAA 835 transaction also includes explanation of benefits information related to adjudicated claims and services.

In response to receiving the HIPAA 835 transaction from insurance company 21, medical office 301 sends a HIPAA 837 transaction that includes coordination of benefits information to the next payer assigned to person 10, insurance company 25.

In response to receiving the HIPAA 837 transaction from medical office 301, insurance company 25 sends a HIPAA 835 transaction that explains an adjudication ruling based on a contract between medical office 301 and insurance company 25, and a contract between person 10 and insurance company 25 (person 10's eligibility and benefits) and the resulting adjudication by the primary insurance company 21.

In response to receiving the HIPAA 835 transaction from insurance company 25, medical office 301 sends a HIPAA 837 transaction that includes coordination of benefits information to the next payer assigned to person 10, payment system 400, with all the previous payer's information in the coordination of benefits segments of the transaction.

In response to receiving the HIPAA 837 transaction, payment system 400 checks the information in the message against unpaid appointments within payment system 400. If a match is found in that the HIPAA 837 transaction states that payment system 400 is the payer associated with the transaction, that the provider who rendered the services is the provider for the appointment, and the subscriber and patient in the transaction are the account holder and patient in payment system 400, then the HIPAA 837 transaction and the appointment are deemed to have been matched.

In response to receiving the HIPAA 837 transaction, payment system 400 then uses the patient outstanding balance information within the HIPAA 837 transaction to either;

1) Charge person 10's credit card for the outstanding balance, or

2) Send a detailed bill to the person 10 via email to explain the outstanding balance and allow person 10 to click on a 'Pay Now' button to have the outstanding amount charged to their existing credit card within payment system 400.

If payment system 400 is successful in collecting the outstanding charges, the services within the HIPAA 837 transaction are deemed to be paid. If the charges are declined by the credit card issuing bank, then the services are deemed to be denied as if the patient is ineligible. If the person 10 does not press the 'Pay Now' button then the services are deemed to be denied as the charges could not be authorized for collection. In response to the services being denied, the medical office may bill person 10 for an amount corresponding to the denied service as defined in the 835 response.

On a periodic basis, payment system 400 processes all the HIPAA 837 transactions for a specific medical office in a settlement process. During settlement, payment system 400 determines if the transactions have been matched and payment status determined; it will also determine whether enough time has passed for the payments collected to have been deposited into the payment collection vendors merchant account. If these conditions are met, payment system 400 aggregates all the payments for medical office 301 since the last settlement cycle and constructs a HIPAA 835 transaction to send to the medical office 301 PMS, The HIPAA 835 transaction is then submitted to medical office 301 either directly or via a clearing house, and either a check or an EFT payment is provided to the medical office as payment for the services included in the HIPAA 835.

If the medical office PMS system is able to process electronic 835 transactions automatically, the medical office PMS system will accept the HIPAA 835 transaction from payment system 400 and auto-post it into the patient's account. Otherwise, the medical office staff manually posts the transactions just as for the 835 transactions from other payers.

In other words, medical office 301 activates circuitry that receives a message in HIPAA 835 format, the message including element CLP05, which is one type of field. Medical office 301 also activates circuitry that makes a determination of whether to send a message in HIPAA 837 format, depending on content of element CLP05. The HIPAA 837 format message includes an element indicating an identity of a patient, an element indicating a date on which a health service was performed for the patient, and an element indicating the health service.

Medical office 301 activates circuitry that sends a message in. HIPAA 270 format, the message including an element indicating an identity of a patient, and another element (element DTP) indicating a proposed date for performing a health service for the patient.

Insurance company 21 provides payment services by paying from an account that is common to a plurality of subscribers. Insurance company 21 receives an HIPAA 270 message from medical office 301. Responsive to the proposed date indicated by the element DTP, insurance company 21 constructs a HIPAA 271 format message including element EB01 indicating whether a patient is eligible to have a payment made on the patient's behalf.

Insurance company 21 receives a HIPAA 837 format message form medical office 301. Responsive to the HIPAA 837 message, Insurance company 21 constructs a message in HIPAA 835 format, such that a content of an element of the HIPAA 835 message depends on whether the insurance company 21 has effected payment.

Payment system 400 electronically receives a message, from medical office 301, in the HIPAA 270 format. Payment system 400 electronically receives a message, from medical office 301, in the HIPAA 837 format. Payment system 400 conditionally electronically charges a payment card account an amount corresponding to a content of the HIPAA 837 message, depending on whether a patient identity indicated by the HIPAA 837 message corresponds to the a patient identity indicated by the HIPAA 270, and whether a date indicated by HIPAA 837 message received in the second format corresponds to a date indicated by the HIPAA 270 message.

Payment system 400 electronically constructs a message in the HIPAA 835 format, such that a content of the HIPAA 835 format message depends on whether payment system 400 electronically charges the payment card account.

In summary, payment system 400 is a patient liability collection system having an interface to a conventional HIPAA compliant medical office, or clearinghouse, acting as a submitter. The interface processes HIPAA transaction messages, to emulate the behavior of an insurance company, but in the pursuit of managing and collecting patient liability for medical services that is not covered by insurance.

Payment system 400 emulates the responses of an insurer such that the practice management system processes the response accordingly. The specific response codes required may differ between practice management systems, but the principle of emulating a response from an insurance company that invokes the correct processing of the practice management system to show the patient as fully paid up or with an outstanding balance is universal.

Thus, there is no change to the legacy software instructions in the submitter; the submitter need only register payment system 400 as a payer. In the case of a patient not relying on insurance to pay the medical office, the registration is that of a primary payer. A person may have insurance but may not be relying on it to pay a certain service with a certain medical office.

In the case of a patient relying on insurance, the registration is that of a secondary payer, so that payment system 400 eventually receives a claim corresponding to patient responsibility. The patient responsibility could be for a co-payment, deductible, co-insurance or a non-covered service, for example.

Payment system 400 and insurance company 21 are non-affiliated, meaning that they are not affiliates with respect to each other. Concerns are affiliates of each other when one concern controls or has the power to control the other, or a third party or parties controls or has the power to control both. Power to control is described in Section 121 of the U.S. regulations of the Small Business Administration.

Payment system 400 and insurance company 25 are non-affiliated.

Payment system 400 and medical office 301 are non-affiliated.

FIG. 2 is a sequence diagram showing sequences of messages and materials exchanged between people, data, and electronic processors in system 1. In FIG. 2, and in each of the other sequence diagrams, each of the rectangles on a dashed line is a process invoked in response to a received message. The process could be facilitated, enabled, or carried out by a computer executing computer instructions to effect a function of the process.

Person 10 registers, or opens an account, with credit card company 28 (message 1010). This act of opening an account may be performed by person 10 by filling out a form provided online by credit card company 28, mailing a paper form to credit card company 28, or speaking on the telephone with a person in credit card company 28 who collects relevant information. An account record now created in credit card company 28 for person 10 includes a billing mailing address, a card expiration date, a security code (CVV) and a card holder name, for example. Credit card company 28 returns a credit card number, expiry date and security code to person 10 (message 1012). Credit card company 28 may also return a physical, plastic credit card.

Subsequently, person 10 registers, or opens an account, with payment system 400 (message 1015). This act of opening an account may be performed by person 10 or office administrator 380 on their behalf by filling out a form provided online by payment system 400, mailing a paper form to payment system 400, or speaking on the telephone with a person in payment system 400 or office administrator 380 who collects relevant information. An account record now created in payment system 400 for person 10 includes the credit card account number received from credit card company 28, a billing mailing address, a card expiration date, and a card holder name. CVV is collected but not stored. Payment system 400 returns the account information (equivalent to a subscriber or member id provided by an insurance company) to person 10 (message 1020) or the office administrator 380.

Payment system 400 stores the credit card information in compliance with the Payment Card Industry Data Security Standard (PCI DSS) v 1.2 or later, based on the National Institute of Standards and Technology (NIST) Advanced Encryption Standard (AES) cryptography technology.

Person 10 purchases an insurance contract from insurance company 21, by supplying information and transferring funds to insurance company 21 (message 1025). Insurance company 21 informs person 10 of an insurance policy information (such as the group number and member id) for person 10 (message 1030).

The spouse of person 10 purchases an insurance contract from insurance company 25 by supplying information and transferring funds to insurance company 25 (message 1035). Insurance company 25 informs the spouse of person 10 of insurance policy information (such as the group number and member id) for person 10 (message 1040). Person 10 is thus a dependent of the spouse of person 10, in the contract with insurance company 25.

Person 10 informs medical office 301 of the policy information received from insurance company 21, the policy information received from insurance company 25, and the account information received from payment system 400 (message 1045), or the office administrator 380 may look up this information in payment system 400.

In response to receiving message 1045, medical office 301 invokes process 305. Process 305 includes setting up a payer list for person 10 ("John Smith") in database 378. FIG. 3 is an image displayed on output screen 370, showing an empty payer list for person 10. FIGS. 4 and 5 are images displayed on output screen 370 at a time subsequent to that depicted in FIG. 3. As shown in FIGS. 4 and 5, person 380 may add insurance company 21 ("Acme Insurance") as a primary payer for person 10.

FIG. 6 is an image displayed on output screen 370, showing "Acme Insurance" in the payer list for person 10.

FIGS. 7 and 8 are images displayed on output screen 370 at a time subsequent to that depicted in FIG. 6. As shown in FIGS. 7 and 8, person 380 adds insurance company 25 ("Beta Insurance") as a secondary payer for person 10.

FIG. 9 is an image displayed on output screen 370, showing "Acme Insurance" and "Beta Insurance" in the payer list for person 10.

FIGS. 10 and 11 are images displayed on output screen 370 at a time subsequent to that depicted in FIG. 9. As shown in FIGS. 10 and 11, person 380 adds payment system 400 ("Z Payer") as a tertiary payer for person 10.

Figure 33:
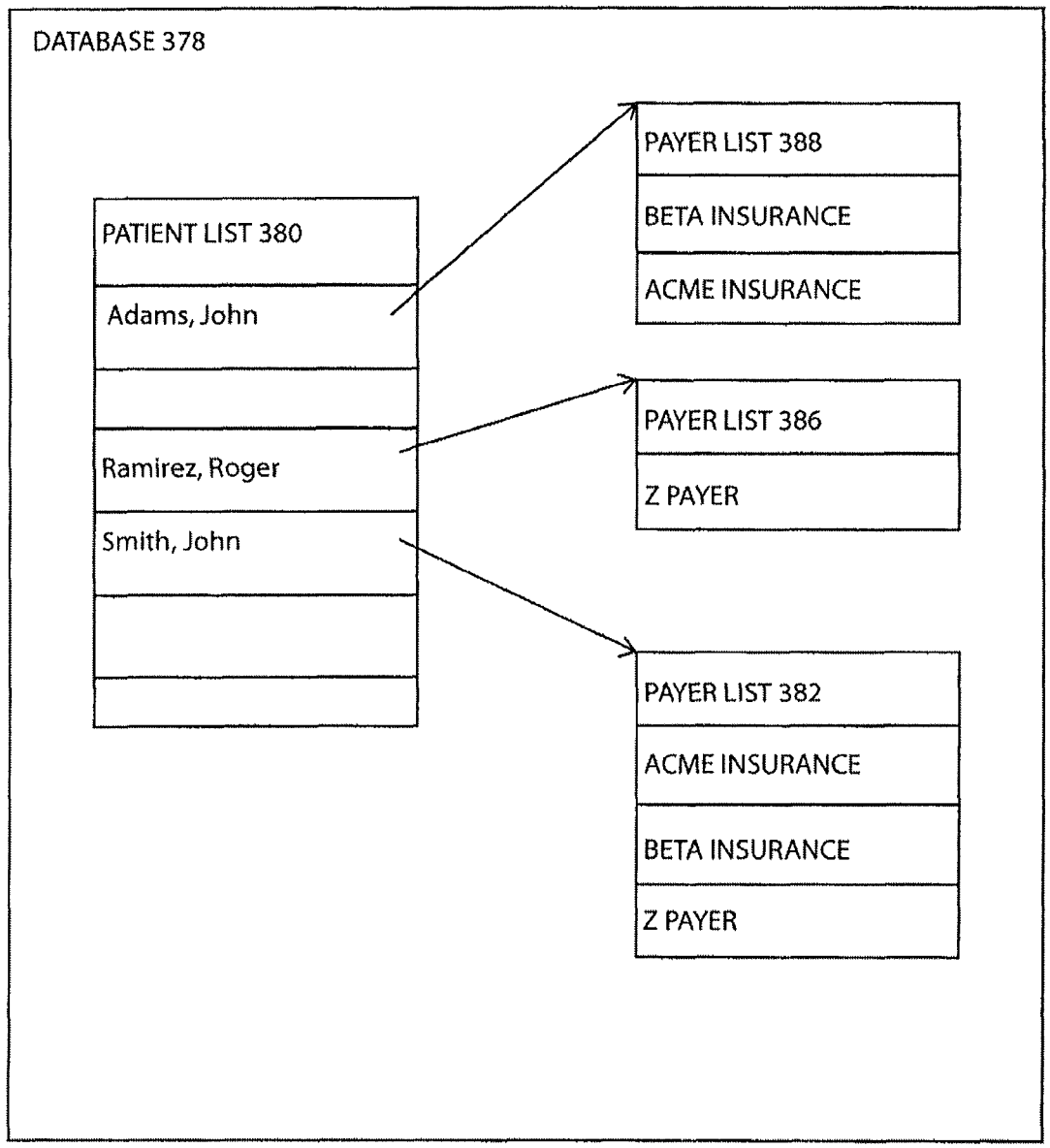
FIG. 33 is a diagram showing a data structure.

FIG. 12 is an image displayed on output screen 370, showing "Acme Insurance", "Beta Insurance" and "Z Payer" in the payer list for person 10. FIG. 33 shows a memory data structure, including payer list 382, corresponding to the image in FIG. 12.

Figure 13:
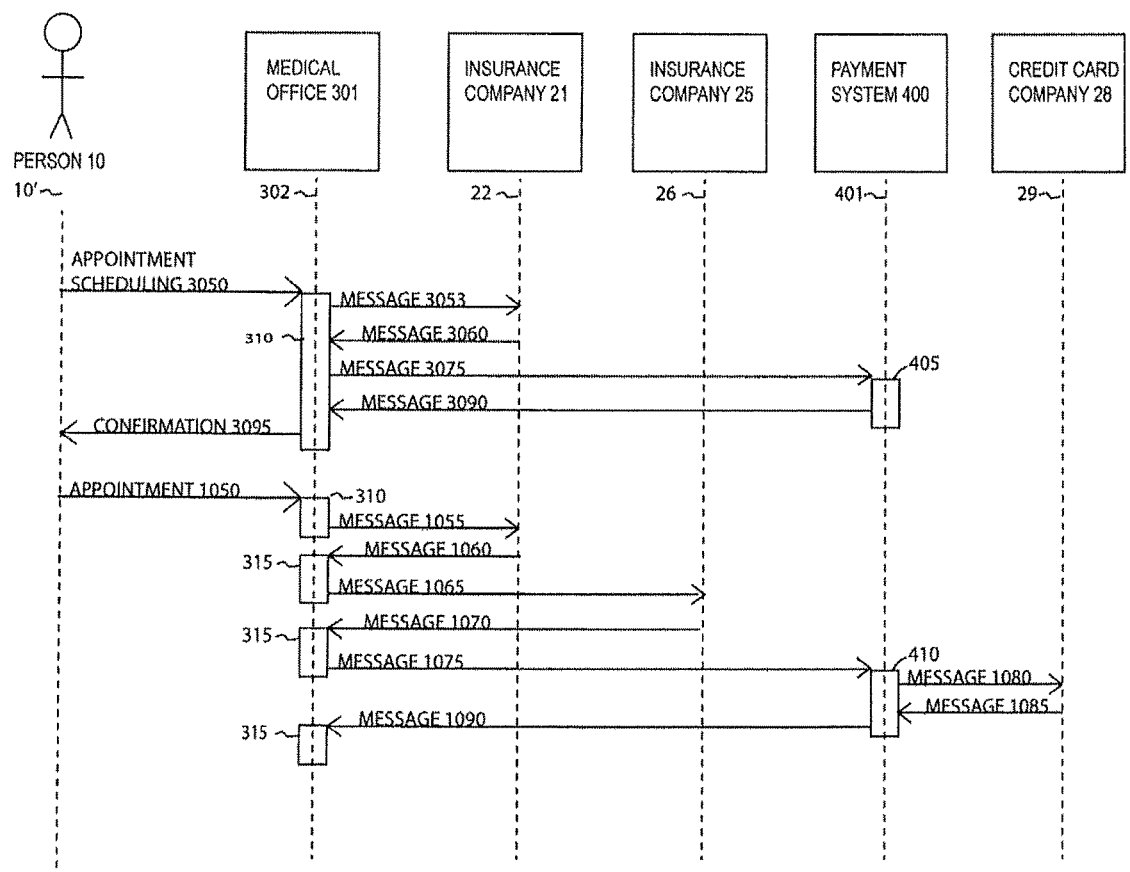
FIG. 13 shows another sequence of messages in system 1.

FIG. 13 shows a process wherein person 10 requests an appointment with medical office 301 (appointment scheduling 3050).

Responsive to the request from person 10, staff in medical office 301 invokes computer program 317 (FIG. 14) to send a message 3053 to determine patient eligibility in insurance company 21. Message 3053 includes a HIPAA 270 transaction, including information regarding the appointment, such as the appointment date, the patient name and ID and subscriber name and ID and expected services to be performed.

FIG. 15 shows message 3053 in more detail.

Responsive to receiving message 3053, insurance company 21 generates message 3060, which is a HIPAA 271 transaction to respond to the HIPAA 270 inquiry, thereby informing medical office 301 regarding eligibility for services.

FIG. 16 shows message 3060 in more detail.

Responsive to the appointment request from person 10, staff in medical office 301 invokes computer program 317 (FIG. 14) to send a message 3075 to determine patient eligibility in payment system 400. Message 3075 includes a HIPAA 270 transaction, including information regarding the appointment, such as the appointment date, the patient name and ID, the account holder name and ID, and expected services to be performed.

FIG. 17 shows message 3075 in more detail. FIG. 17 is relatively abstract, compared to actual text of message 3075 shown in FIG. 38 below.

Responsive to receiving message 3075, payment system 400 generates message 3090, which is a HIPAA 271 transaction to respond to the HIPAA 270 inquiry, thereby informing medical office 301 regarding whether person 10 is set up in system 400 with a valid payment method (i.e. are they eligible based on the information system 400 has at present).

If person 10 is already set up in payment system 400 and the payment card account of person 10 is valid, then the payment system 400 will automatically set up an appointment record for person 10 based on the information in the HIPAA 270.

Figure 18:
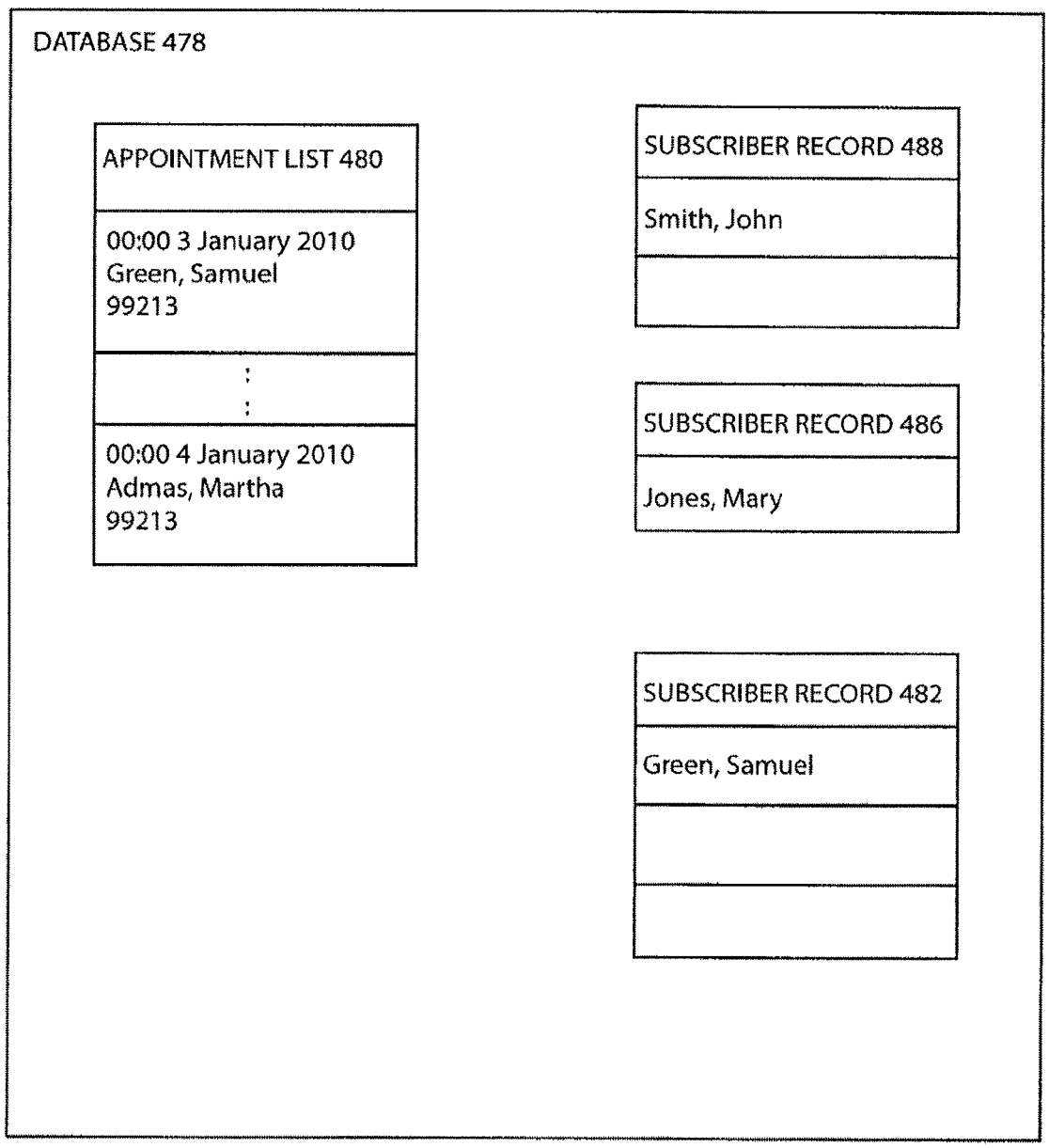
FIG. 18 is a diagram showing a data structure storing predicted appointments for health care.

FIG. 18 shows appointment list 480 in payment system 400 before payment system 400 receives the message 3075.

Figure 19:
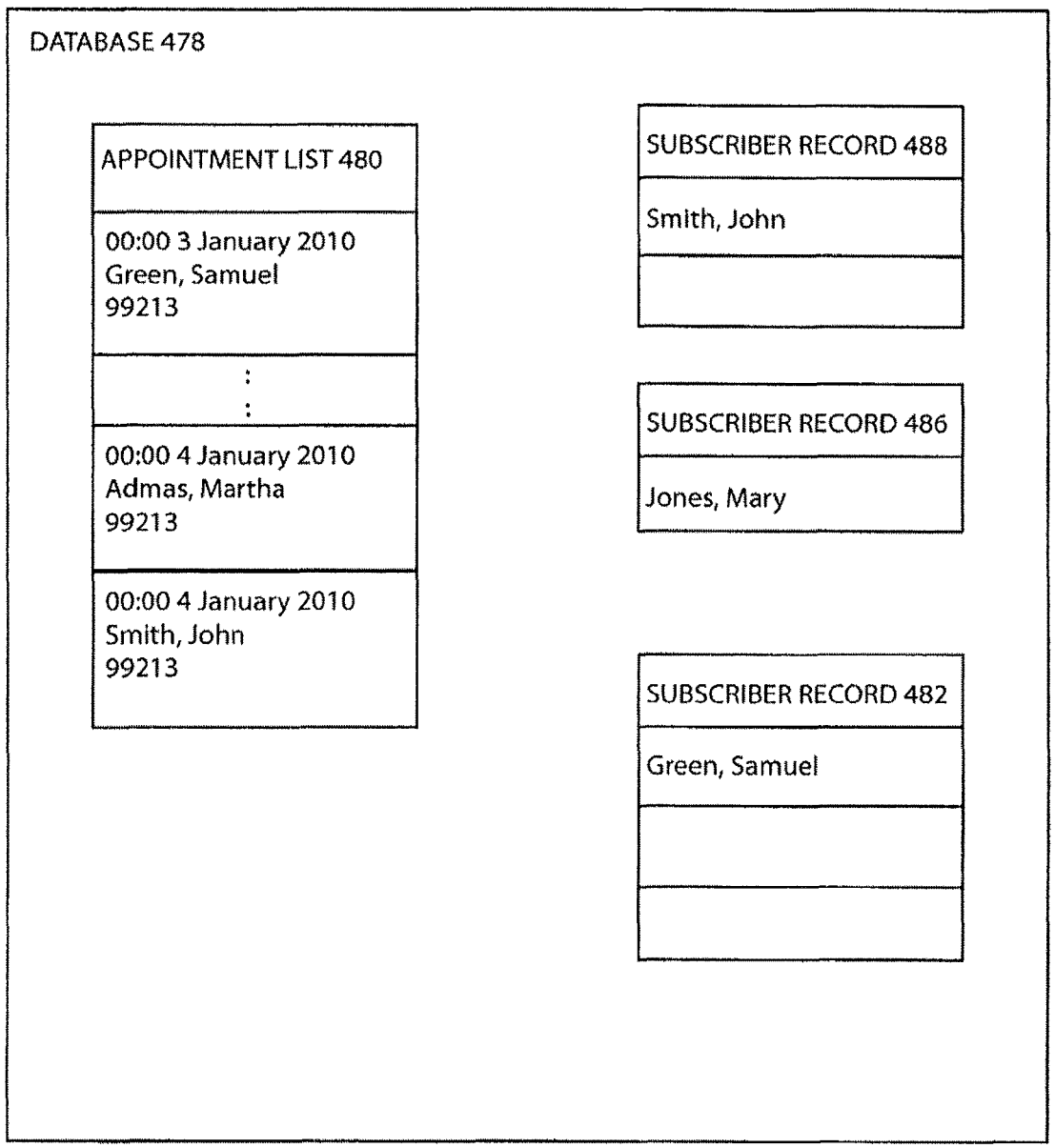
FIG. 19 is a diagram showing a data structure storing predicted appointments for health care, at a time after that shown in FIG. 18.

FIG. 19 shows appointment list 480 in payment system 400 after payment system 400 receives the message 3075, in the case where person 10 is already set up in payment system 400 and the payment card account of person 10 is valid.

If person 10 is not already set up in payment system 400 or the payment card account of person 10 is not valid, then payment system 400 sets up the appointment and sends an email to person 10, enabling person 10 to either register or update their payment card prior to the appointment with medical office 301.

FIG. 20 shows message 3090 in more detail.

In summary, system 400 emulates an insurance company to use HIPAA 270/271 transactions to communicate appointment scheduling information between the payment system 400 and the medical office practice management system without requiring any changes to the legacy code. As such the personnel at medical office 301 do not need to set up appointments directly within payment system 400.

Figure 14:
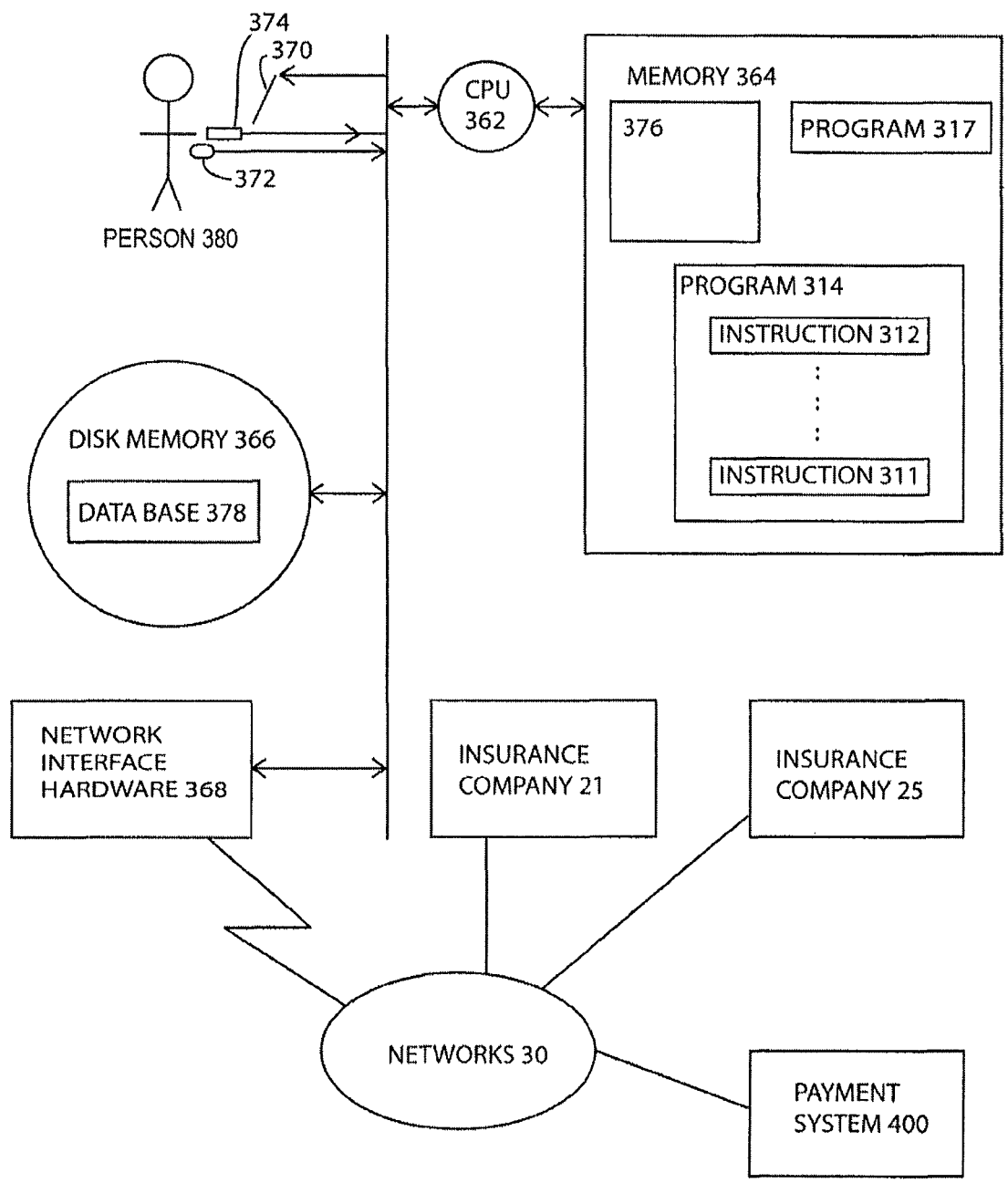
FIG. 14 is a diagram showing circuitry in the system 1.

Person 10 visits medical office 301 for an appointment and receives a medical service. An appointment 1050 to the medical office 301 produces charges. As shown in FIG. 14, person 380 may actuate mouse 372 and keyboard 374 to enter the charges, thereby invoking computer process 310, which sends a HIPAA 837 transaction (message 1055) to insurance company 21. Subsequently, insurance company 21 adjudicates (determines) the payment obligation of insurance company 21 and patient 10. Subsequently, insurance company 21 constructs a HIPAA 835 transaction (message 1060) containing an adjudicated result generated by insurance company 21. Subsequently, insurance company 21 sends the HIPAA 835 transaction (message 1060) to medical office 301. Insurance company 21 sends payment, corresponding to insurance company 21 payment obligation based on the adjudicated result generated by insurance company 21, to medical office 301.

Responsive to receiving message 1060, medical office 301 invokes computer process 315, which constructs and sends a HIPAA 837 transaction to insurance company 25 (message 1065) based on the received HIPAA 835 transaction (message 1060).

Subsequently, insurance company 25 adjudicates (determines) the payment obligation of insurance company 25. Subsequently, insurance company 25 constructs a HIPAA 835 transaction (message 1070) containing an adjudicated result generated by insurance company 25. Subsequently, insurance company 25 sends the HIPAA 835 transaction (message 1070) to medical office 301. Insurance company 25 sends payment, corresponding to insurance company 25 payment obligation based on the adjudicated result generated by insurance company 25, to medical office 301.

Responsive to receiving message 1070, medical office 301 invokes computer process 315, which constructs and sends a HIPAA 837 transaction to payment system 400 (message 1075) based on the received HIPAA 835 transaction (message 1070).

Responsive to receiving the HIPAA 837 transaction (message 1075), payment system 400 invokes computer process 410, determines the patient's outstanding responsibility and sends a charge request (message 1080) for that amount to credit card company 28. Credit card company 28 determines whether to accept the charge and sends the result of the determination (message 1085) to payment system 400.

Responsive to receiving message 1085, payment system 400 constructs and sends a HIPAA 835 transaction (message 1090) based on the message received from credit card company 28 (message 1085).

FIG. 21 shows an output screen image for entering a claim for payment for medical services rendered. FIG. 22 shows a report detailing payments received from various payers. As shown in FIG. 22, a report is generated in which, in this case, the patient responsibility for person 10 is 0.

Figure 23:
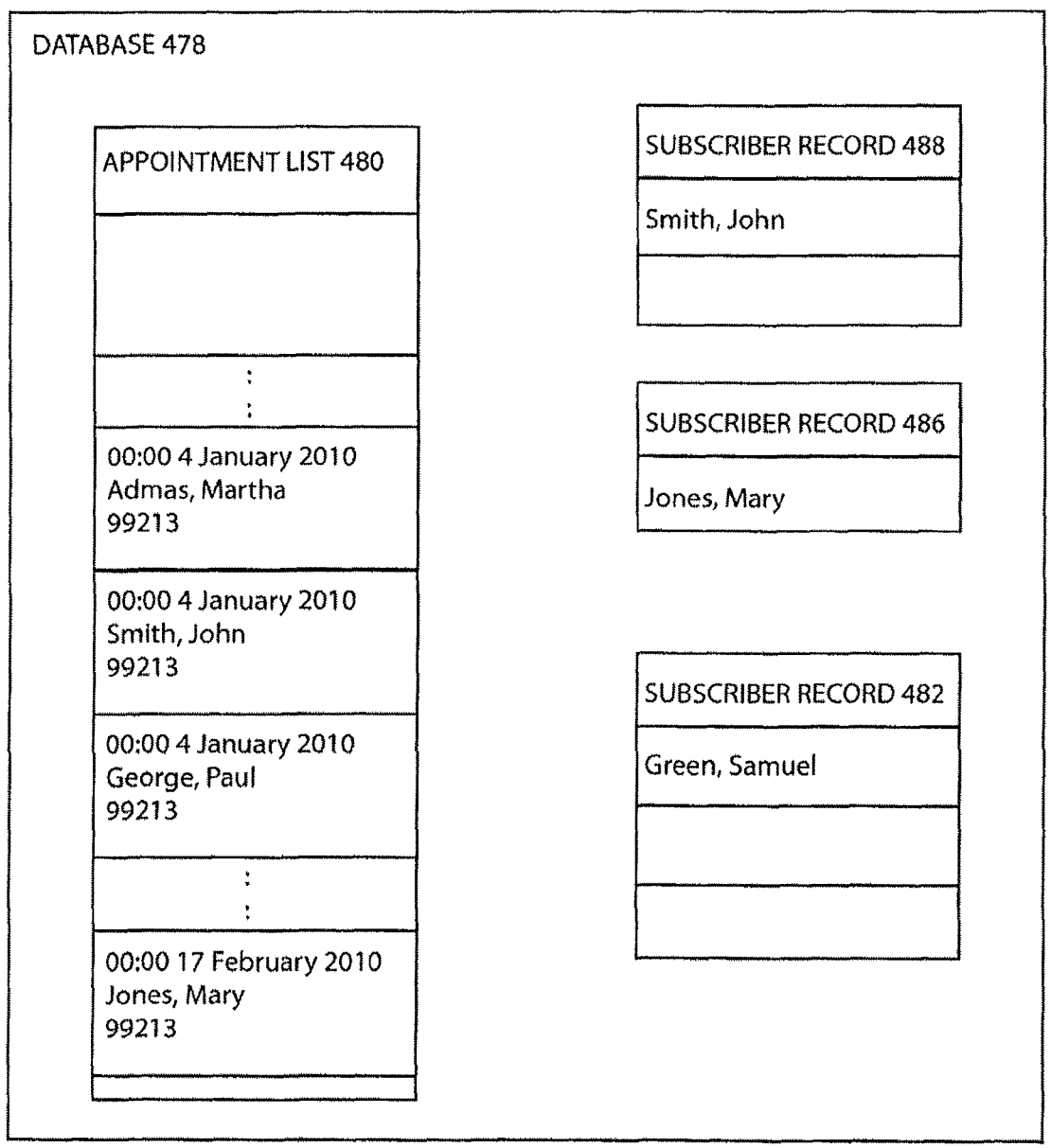
FIG. 23 is a diagram showing a data structure storing predicted appointments for health care.

FIG. 23 shows appointment list 480 at the time that payment system 400 receives the message 1075. In contrast to FIG. 19, FIG. 23 shows appointments added for other people since creation of the appointment record for person 10 (John Smith). FIG. 23 also reflects appointment records that have been removed since the creation of the appointment record for John Smith.

Figure 24:
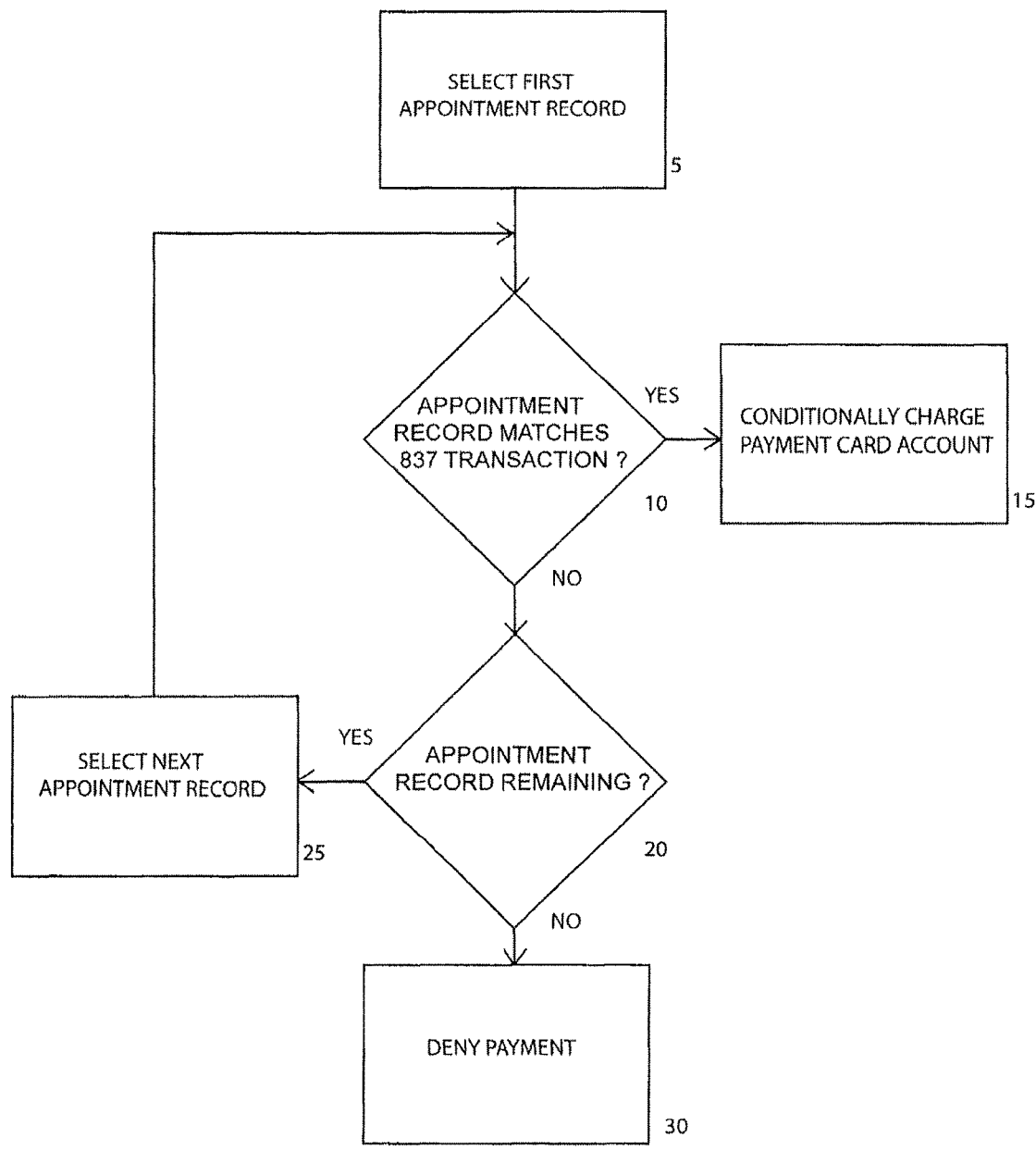
FIG. 24 is a flowchart describing a process shown in the system 1.

FIG. 24 is a flowchart showing process 410. CPU 462 selects the first appointment record in appointment list 480 (step 5). CPU 462 determines whether the current appointment record matches the HIPAA 837 transaction (step 10). If the appointment record does match the HIPAA 837 transaction, CPU 462 conditionally charges the payment card account (step 15).

If the current appointment record does not match the HIPAA 837 transaction, CPU 462 determines whether there are appointment records remaining in appointment list 480 (step 20). If there are appointment records remaining in appointment list 480, CPU 462 selects the next appointment record (step 25) and resumes processing at step 10.

If step 20 determines there are no appointment records remaining in appointment list 480, CPU 462 constructs a HIPAA 835 transaction to indicate that payment is denied.

Step 10 includes checking whether the appointment record currently under consideration is unpaid, determining whether the HIPAA 837 transaction states that payment system 400 is the payer associated with the transaction, determining whether the provider who rendered the services is the provider for the appointment, and determining whether the subscriber and patient in the 837 transaction are the account holder and patient in payment system 400.

Step 10 also may include searching for services in the HIPAA 837 transaction having a corresponding service in the appointment record. Two services correspond if they have the same service code. Alternatively, two services correspond if they are sufficiently similar. For example, in system 400 the service having service code 99213 may correspond to the service having service code 99214.

Step 15 includes determining if payment was collected. If payment was collected, the service is deemed to be paid at a discounted fee set up by medical office 301 in the payment system 400. If system 400 finds a service in the HIPAA 837 transaction having a corresponding service in the appointment record, and the charges were declined by person 10's credit card issuing bank, the charges may be attempted again, and if the charges are still declined then the service is deemed to be denied as if person 12 was not eligible at the time of service and the patient responsibly is set to a non-discounted fee set up in payment system 400.

If step 10 does not find a service in the HIPAA 837 transaction having a corresponding service in the appointment record, then there is no match, and processing proceeds to step 20.

If the service is deemed to be paid, then the transaction fee related to using the payment system 400 is set as an adjustment to the collected funds.

Step 15 includes using the patient outstanding balance information within the HIPAA 837 transaction to either:

1) Charge person 10's credit card for the outstanding balance, or

2) Send a detailed bill to the person 10 via email to explain the outstanding balance and allow person 10 to click on a 'Pay Now' button to have the outstanding amount charged to their existing credit card within payment system 400.

If payment system 400 is successful in collecting the outstanding charges, the services within the HIPAA 837 transaction are deemed to be paid. If the charges are declined by the credit card issuing bank then the services are deemed to be denied as if the patient is ineligible. If the person 10 does not press the 'Pay Now' button then the services are deemed to be denied as the charges could not be authorized for collection. In response to the services being denied, the medical office may bill person 10 directly for full outstanding patient responsibility corresponding to the denied service as defined in the 835 response.

Responsive to receiving message 1085, payment system 400 constructs and sends a HIPAA 835 transaction (message 1090) based on the message received from credit card company 28 (message 1085).

In summary, payment system 400 is a patient collection system having an interface to a conventional HIPAA compliant medical office, or clearinghouse, acting as a submitter. The interface processes HIPAA transaction messages, to emulate the behavior of an insurance company, but in the pursuit of managing and collecting patient liability for medical services that is not covered by insurance.

Payment system 400 emulates the responses of an insurer such that the practice management system processes the response accordingly. The specific response codes required may differ between practice management systems, but the principle of emulating a response from an insurance company that invokes the correct processing the practice management system to show the patient as fully paid up or with an outstanding balance is universal.

Thus, there is no change to the legacy software instructions in the submitter; the submitter need only register payment system 400 as a payer. In the case of a patient not relying on insurance to pay the medical office, the registration is that of a primary payer. A person may have insurance but may not be relying on it to pay a certain service with a certain medical office.

In the case of a patient relying on insurance, the registration is that of a secondary payer, so that payment system 400 eventually receives a claim corresponding to patient responsibility. The patient responsibility could be for a co-payment, deductible, co-insurance or a non-covered service, for example.

Central processing unity (CPU) 362 (FIG. 30) executes program 314 (a plurality of computer instructions) to effect process 315. Program 314 includes a programming construct that waits for and dispatches messages received from computer networks 30. When the programming construct receives a HIPAA message, the programming construct calls the relevant program ("dispatches the message"), as shown in steps 10, 15, and 20 of FIG. 22.

Figure 25:
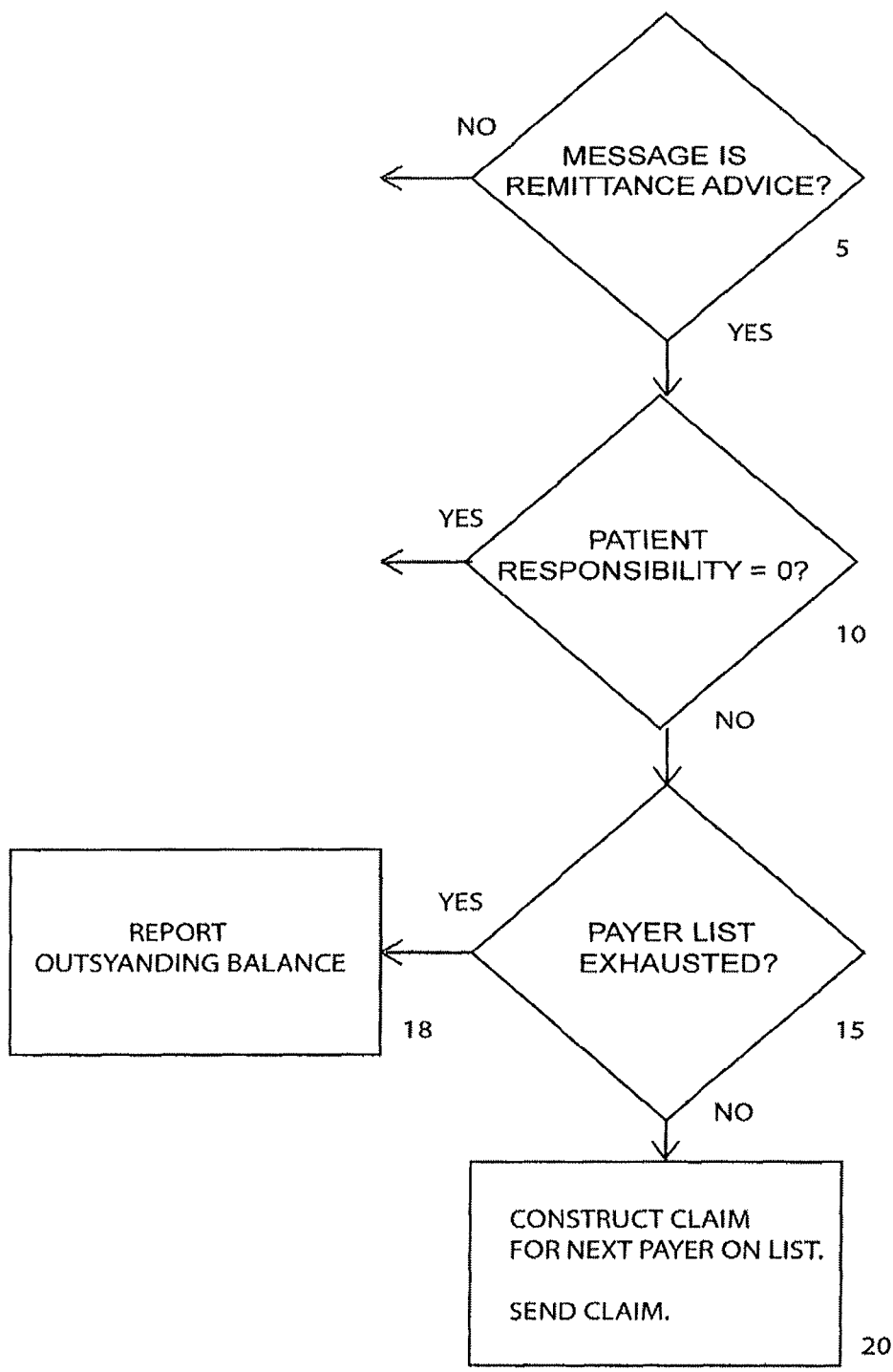
FIG. 25 is a flowchart describing a process shown in FIG. 13.

FIG. 25 is a flowchart showing process 315. CPU 362 determines whether a message, received via networks 30, is a HIPAA 835 transaction (step 5). If the received message is a HIPAA 835 transaction, CPU 362 determines whether the CLP05 element value is not present or (FIG. 27) is equal to zero and that there are no patient responsibility (PR) adjustments in the service adjustment segment (CAS) (step 10). If the patient responsibility element is not zero, meaning that costs have not been fully paid, CPU 362 determines whether there are any payers remaining in payer list 382 (step 15). If there are payers remaining in payer list 382, CPU 362 constructs a HIPAA 837 transaction with the information in the 835 response as coordination of benefits information within the HIPAA 837 transaction. CPU 362 sends the HIPAA 837 transaction to the next payer, via network interface hardware 368 and networks 30 (step 20). If there are no payers remaining in the payer list 382, the outstanding balance is reported (step 18).

The paid amount and the billed amount typically do not match. In general the paid amount is lower than the billed amount and then a series of adjustments are noted that balance it out.

In summary, system 1 employs existing standard insurance based electronic transactions (HIPAA transactions) to manage the collection and payment of the patient portion of medical bills. For example, system 1 generates a standard 837 EDI transaction to allow a practice management system in a medical office to send a request for payment of patient collections, or a request to collect outstanding patient collections. Payment system 400 then generates a standard HIPAA 835 transaction to report whether the collection was made and how much was collected. Since system 1 employs standard transactions, the payment system and the medical office's practice management system are able to interact without any specialized IT changes.

FIGS. 26A and 26B show message 1055 (FIG. 13) in more detail. Message 1055 includes an element CLMO2 ("Billed Amount for Claim") having the value $217.53. The insurer adjusts this amount to the allowed amount which is the negotiated rate between the insurer and the medical office. The billed amount is the same regardless of who the medical office sends the claim to and is sometimes referred to as the retail amount.

FIG. 27 shows message 1060 in more detail. Message 1060 includes an element CLPO4 ("Claim Payment Amount") having the value $151.43, which is the amount that insurance company 21 ("Acme Insurance") is paying on the claim. Message 1060 also include information about how the insurance company has adjusted the claim from the billed amount to the paid amount, including element CAS03 ("Contractual Obligations") ($46.10) and element CAS03 ("Patient Responsibility") ($20.00).

Responsive to receiving message 1060, CPU 362 executes program 314, which constructs and sends a HIPAA 837 transaction to insurance company 25 (message 1065) based on the received HIPAA 835 transaction (message 1060).

FIGS. 28A, 28B show message 1065 in more detail. Message 1065 retains that CLMO2 element "Billed Amount for Claim" having the value $217.53, but details out the allowed amount that can be paid out on this claim (LOOP 2320 AMT COB Allowed Amt=$171.43), what has already been paid out (LOOP ID 2430 SVD02 Service Line Paid Amt=$151.43), and the outstanding patient responsibility amount (LOOP ID 2430 CAS03 Patient Responsibility-320.00). Insurance company 25 uses this information together with their contract with patient 10 to determine if they should pay out any of the outstanding patient responsibility.

FIG. 29 shows message 1070 in more detail. Message 1070 includes an element CLPO4 having the value $10.00, which is the amount that insurance company 25 ("Beta Insurance") is paying on the claim.

Responsive to receiving message 1070, CPU 362 executes program 314, which constructs and sends a HIPAA 837 transaction to payment system 400 (message 1075) based on the received HIPAA 835 transaction (message 1070).

FIGS. 30A, 30B show message 1075 in more detail. Message 1075 includes an element "Billed Charges for Claim" having the value $217.53, and includes all the payments, adjustments and patient responsibilities determined by insurance company 21 and 25.

FIGS. 30A, 30B are relatively abstract, compared to actual text of message 1075 shown in FIG. 45 described below.

FIG. 31 shows message 1090 in more detail. Message 1090 includes an element CLPO4 having the value $9.00, which is the amount that payment system 400 ("Z Payment Company") collects from person 10's credit card, via credit card company 28 minus the fee charged by Z Payment Company for collection. In other words, person 10's credit card was charged $10.00, Z Payment Company retained a $1.00 fee for collecting this charge, and so the amount paid to Good Life Medical Clinic is $9.00.

Responsive to receiving message 1090, CPU 362 executes program 314 to determine if the claim has been paid in full.

Figure 32:
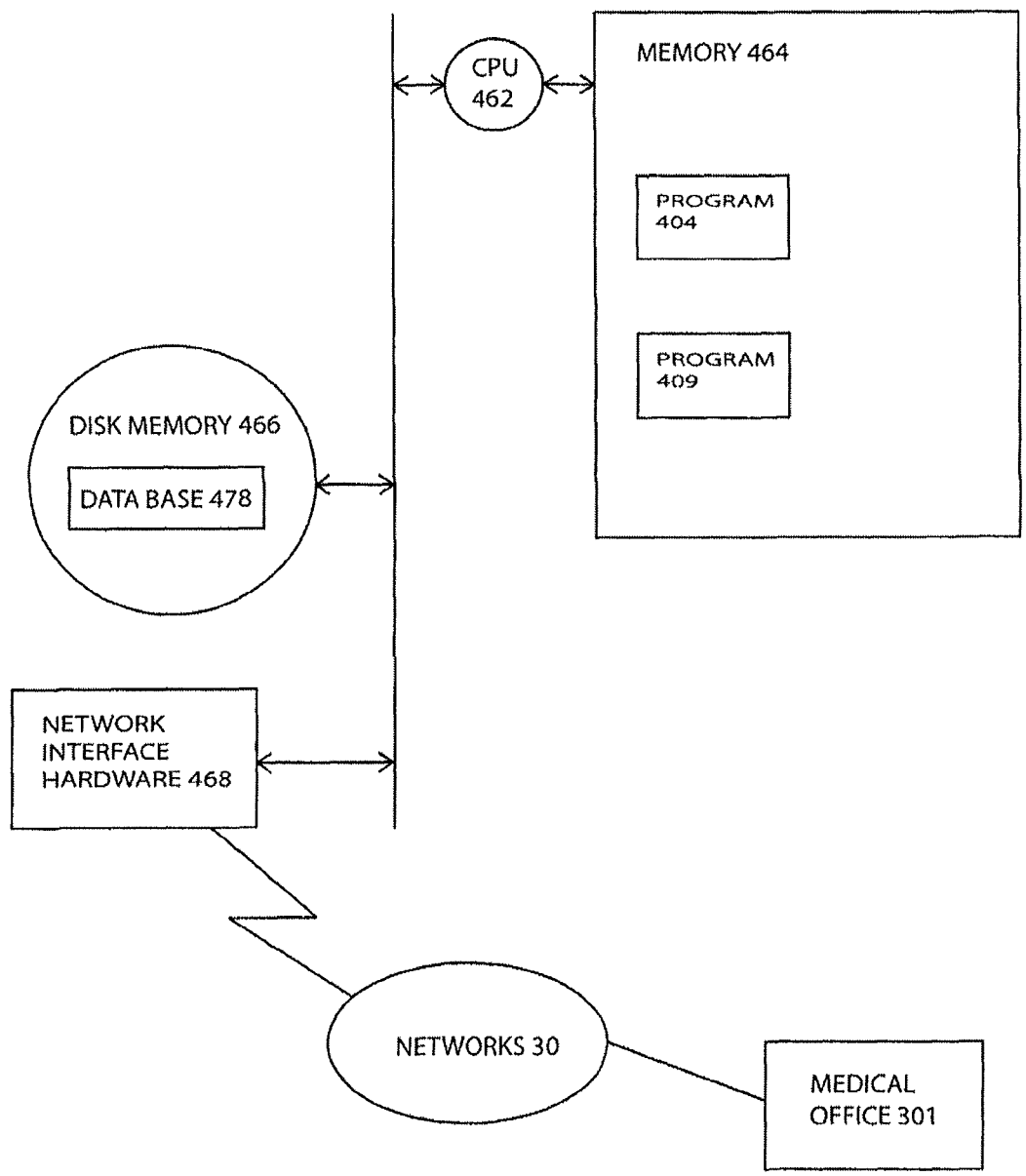
FIG. 32 is a diagram showing circuitry in the system 1.

FIG. 32 shows another aspect of payment system 400. A computer system includes central processing unit (CPU)

462, random access memory 464, disk memory 466 for storing programs and data, and network interface hardware 468.

CPU 462 executes programs stored in memory 464, to process received messages, and to generate and send messages from payment system 400.

Database 478 is stored on magnetic disk 466, and portions of database 478 are read into memory 464 as needed.

CPU 462 executes program 404 (a plurality of computer instructions) to effect process 405. CPU 462 executes program 409 (a plurality of computer instructions) to effect process 410.

In summary, medical office 301 activates circuitry that receives a message in a HIPAA 835 format message including element CLP05. Element CLP05 is a type of field.

Medical office 301 also activates circuitry that makes a determination of whether to send a HIPAA 837 format message depending on a content of the CLP05 element of a message received by the circuitry described in the previous paragraph. The HIPAA 837 message includes a code identifying a medical service for a patient.

Insurance company 21 receives a HIPAA 837 message from medical office 301 and, in response, constructs a HIPAA 835 format message having a CLP05 element having a content depending on an insurance contract.

Payment system 400 receives a HIPAA 837 format message from medical office 301 and, in response, constructs a HIPAA 835 format message having a CLP05 element having a content depending on whether a payment card account is chargeable at a time after the medical service is performed.

With further reference to FIG. 14, another aspect of medical office 301 is shown. An administrator station includes an IBM compatible PC having CPU 362, random access memory 364, disk memory 366 for storing programs and data, and network interface hardware 368. The administrator station also includes a user interface having a display 370, a keyboard input device 374, and a mouse input device 372.

Processor 362 executes program 376 and program 314 stored in memory 364 to generate and send messages from medical office 301.

Database 378 is stored on magnetic disk 366, and portions of database 378 are read into memory 364 as needed.

FIG. 33 shows database 378 in more detail. Database 378 includes patient data structure 380, which may be conceptualized as a list of patients. Each entry in patient list 380 includes a reference to a payer list, such as payer list 382 for person 10 (John Smith), payer list 386 for Roger Ramirez, or payer list 388 for John Adams.

In the data structures shown in the Figures, lines represent a reference, such as a pointer, between one element and another. These references are not necessarily direct memory address pointers. Instead, more generally, each reference is a data entity, stored in association with one (referencing) element, that enables a processor to find a related (referenced) element. To physically address the referenced element, the processor may subject the reference to various translations or mappings. In the case of the reference to payer list 382, the reference may be simply a list of the names, or identification codes, of the three payers.

Each entry in a payer list, such as payer list 382, includes connectivity information allowing communication through networks 30. The connectivity information may be a payer id assigned by a clearinghouse, a U.S. federal tax ID, or some other type of national ID, for example.

From an EDI perspective of payment system 400, one can either directly connect to all the participating providers, or one can rely on a clearing house such as an Emdeon clearinghouse. In the latter case, payment system 400 receives HIPAA 837 transactions from the clearinghouse that are directed to the payer ID of payment system 400 (which is given to the providers so they can set up payment system 400 in their respective PMSs), and payment system 400 sends HIPAA 835 transactions to the clearinghouse, which uses a tax id and/or the national provider id to route the transaction to the right provider. The clearinghouse therefore works as a kind of post office that gets the right transactions to the right recipients in the correct format.

Instead of operating via a clearinghouse, each entry in payer list 382 may include a Universal Resource Locator (URL), such as http://www.metlife.com:234, corresponding to a payer. This could also be FTP or other EDI communications networks such as AS/2

In summary, system 1 includes insurance company 25, which is a type of entity that provides insurance services. These services involve a contract whereby, for specified consideration, insurance company 25 undertakes to compensate others for costs relating to a particular subject as a result of the occurrence of designated events, such as prescribed medical procedures.

Medical office 301 controls execution of computer instruction 311, which acts to send message 1065 (FIG. 13) to insurance company 25, message 1065 including data (FIGS. 28A, 28B, element SV1) encoding a medical service for a person.

Medical office 301 controls execution of computer instruction 312 (FIG. 16), which acts to receive message 1070 in reply to message 1065.

A CPU 462 (FIG. 32) executes computer instructions 409 to effect a process for operating with medical office 301, the process including the step of receiving a message, such as message 1075, from computer instruction 311.

Responsive to the receiving step, CPU 462 and computer instructions 409 send messages, such as message 1090, to computer instruction 312. Message 1090 encodes a monetary amount (FIG. 31, field CLP05) collectable from the person in response to a service performed by medical office 301.

Figure 34:
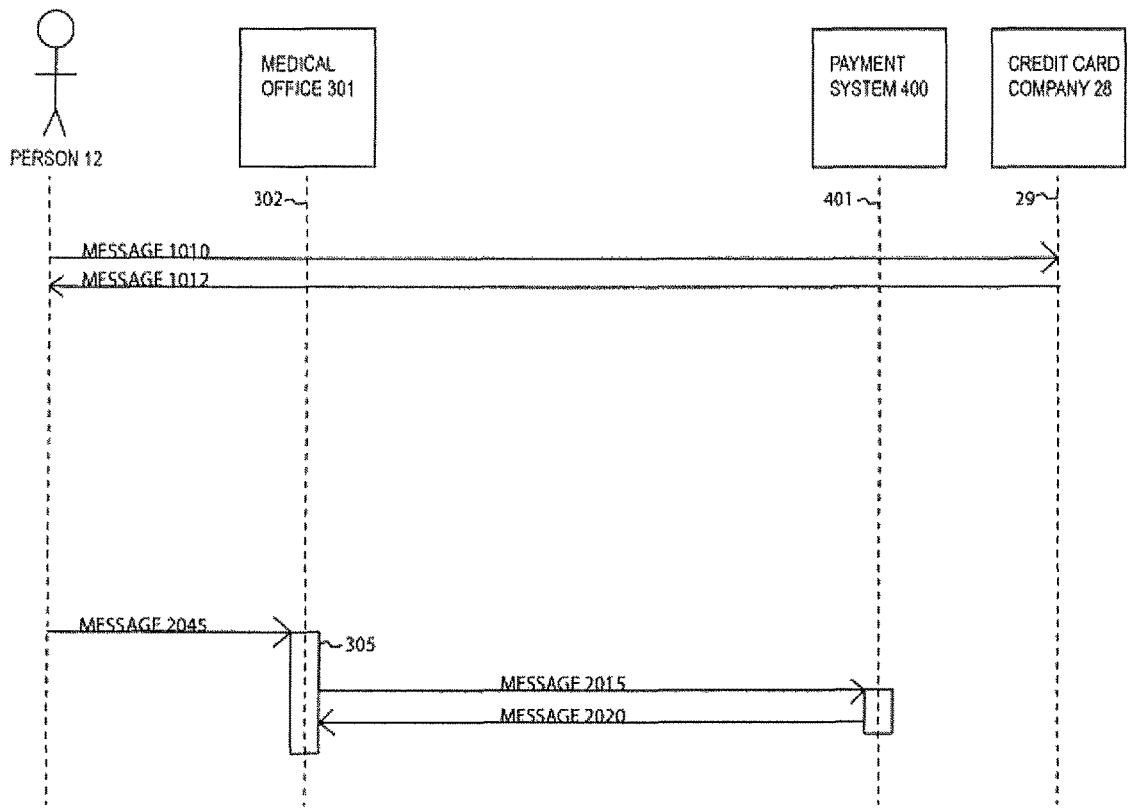
FIG. 34 shows a sequence of messages in system 1.

FIG. 34 is a diagram showing sequences of messages and materials exchanged between people, data, and electronic processors in system 1 in accordance with another embodiment. Person 12 is self-paying, meaning that person 12 is not relying on a health insurance policy to pay for the medical service cited in the example. Person 12 may be self-paying because, for example, person 12 has no medical insurance. Alternately, person 12 may be self paying because, for example, medical office 301 is not contracted with the insurance carrier of person 12, such that the medical office 301 is out of network.

Person 12 registers, or opens an account, with credit card company 28 (message 1010). An account record now created in credit card company 28 for person 12 includes a billing mailing address, a card expiration date, and a card holder name. Credit card company 28 returns a credit card number, expiry date, and possibly a security code to person 12 (message 1012). Credit card company 28 may also return a physical, plastic credit card.

Person 12 informs medical office 301 of the account number received from credit card company 28 (message 2045).

Subsequently, medical office 301 registers, or opens an account for person 12, in payment system 400 (message 2015). Message 2015 includes the credit card number of person 12 received from credit card company 28. An account record now created in payment system 400 for person 12 includes the credit card number received from credit card company 28 (stored in a PCI complaint manner) and a mailing address. Payment system 400 returns an account number to medical office 301 (message 2020).

Figure 35:
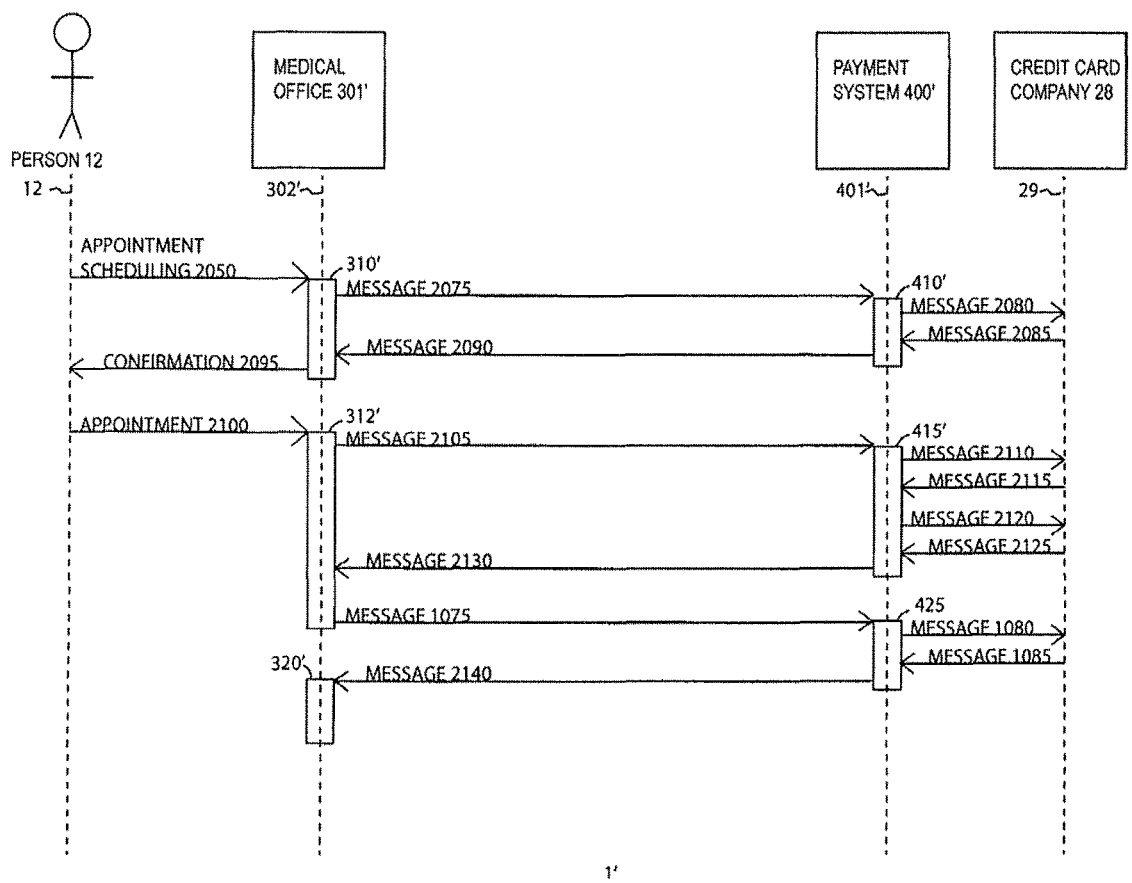
FIG. 35 shows another sequence of messages.

FIG. 35 shows a process wherein person 12 requests an appointment with medical office 301' (appointment scheduling 2050).

Responsive to the appointment request from person 12, staff in medical office 301' invokes computer program 317 (FIG. 14) to send a message 2075 to determine patient eligibility in payment system 400'. Message 2075 includes a HIPAA 270 transaction, including information regarding the appointment, such as the appointment date, the patient name and ID, the account holder name and ID, and expected services to be performed.

Responsive to receiving message 2075, payment system 400' generates message 2090, which is a HIPAA 271 transaction to respond to the HIPAA 270 inquiry, thereby informing medical office 301' regarding whether person 12 is set up in system 400' with a valid payment method (i.e. are they eligible based on the information system 400' has at present).

If person 12 is already set up in payment system 400' and the payment card account of person 12 is valid, then the payment system 400' will automatically set up an appointment record for person 12 based on the information in the HIPAA 270, as described above in connection with person 10.

If person 12 is already set up in payment system 400' and the payment card account of person 12 is valid, payment system 400' preauthorizes charges that are known to have to be collected at time of service, against the person 12's credit card prior to the appointment (message 2080 and 2085).

If person 12 is not already set up in payment system 400' or the payment card account of person 12 is not valid, then payment system 400' sends an email to person 12, enabling person 12 to either register or update their payment card prior to the appointment with medical office 301'.

Person 12 visits medical office 301' for the scheduled appointment and receives a medical service (appointment 2100).

Once the appointment is complete, staff of medical office 301' adds any additional services to the service list, and invokes a program to send the service list to payment system 400' (message 2105). In response to receiving message 2105, payment system 400' collects originally scheduled and additional services from the credit card provided by the patient. Payment system 400' first collects the preauthorized amount (messages 2110 and 2115), and then collects any amount for additional services (message 2120 and 2125).

If charges cannot be collected, the medical office staff are encouraged to collect directly from the patient, or bill them later but at the non-discounted rate.

At this point, payment system 400' has collected either all or part of the person 12's responsibility for the appointment and is ready to pay medical office 301' the collected funds.

After person 12 visits medical office 301' for an appointment 2100 and receives a medical service, medical office 301' eventually invokes computer process 312', which constructs and sends a HIPAA 837 transaction to payment system 400' (message 1075). Payment system 400' conditionally processes message 1075 depending, inter alfa, on the contents of appointment list 480, as described above in connection with person 10.

In other words, responsive to receiving message 1075, payment system 400' checks the information in message 1075 against unpaid appointments within payment system 400'. If a match is found in that the 837 transaction states that payment system 400' is the payer associated with the transaction, that the provider who rendered the services is the provider for the appointment, and the subscriber and patient in the transaction are the account holder and patient in payment system 400', then the HIPAA 837 transaction and the appointment are deemed to have been matched.

Once the 837 transaction is matched with an appointment record, payment system 400' searches for services in the 837 transaction having a corresponding service in the appointment record. Two services correspond if they have the same service code. Alternatively, two services correspond if they are sufficiently similar.

If system 400' finds a service in the 837 transaction having a corresponding service in the appointment record, and payment was collected from the person 12, then the service is deemed to be paid at a fee, which may be a discounted fee, set up by medical office 301' in the payment system 400'. If system 400' finds a service in the 837 transaction having a corresponding service in the appointment record, and payment was not collected from the person 12, and the charges were declined by person 12's credit card issuing bank, then the service is deemed to be denied as if person 12 was not eligible at the time of service and the patient responsibility is set to a non-discounted fee set up in payment system 400'.

If system 400' does not find a service in the 837 transaction having a corresponding service in the appointment record, then the service is deemed to be denied as an invalid service in the transaction and the entire billed amount is rejected.

If the service is deemed to be paid, then the transaction fee related to using the payment system 400' is set as an adjustment to the collected funds.

As shown by process 425, payment system 400' processes all the 837 transactions for a specific medical office in a process known as settlement. During settlement the payment system 400' determines if the transactions have been matched and payment status determined; it will also determine whether enough time has passed for the payments collected to have been deposited into the payment collection vendors merchant account. If these conditions are met for an 837 transaction, payment system 400' aggregates all the payments for the medical office since the last settlement cycle and constructs an 835 transaction to send to the medical office PMS. The 835 is then submitted to medical office 301' either directly or via a clearing house (message 2140), and either a check or an EFT payment is provided to medical office 301' as payment for the services included in the 835. If the PMS of medical office 301' is able to process electronic 835 transactions automatically, the PMS will accept the 835 transaction from the payment system 400' and auto-post it into the patient's account. If the PMS is unable to automatically post the 835 then the staff of medical office 301' will manually post the transactions just as they do for the 835 transactions from other payers.

If all payments were collected from the patient then the patient's account will have a zero balance within the medical office PMS and the account will be deemed settled by the medical office. If payment system 400' was unable to collect part or all of the patient's balance, then the medical office PMS will show an outstanding balance and the medical office will process the balance using their standard processes for patient collections.

Provided below is a more detailed description of appointment setup and subsequent process 410' shown in FIG. 35.

1) When a patient requests an appointment, the staff of medical office 301' looks up the patient in the practice management system of medical office 301'.

2) If the patient exists in their practice management system and already has payment system 400' assigned as one of their payers, then the staff sets up an appointment in the practice management system as normal.

3) If the patient exists in the practice management system but does not have payment system 400' assigned as a payer, then they assign payment system 400' as their payer of last resort and enter the patient's email address as the member id for the subscriber responsible for the patient. If the subscriber and the patient are different entities then both the subscriber and the patient are set up in this way.

4) If the patient does not exist in their practice management system, then they need to be set up as usual with the appropriate subscriber/patient relationships if necessary. The member id for the subscriber will be their email address; no member id is assigned to the patient at this stage.

5) In batch or real time mode, medical office 301' generates a HIPAA 270 transaction and sends the HIPAA 270 transaction to payment system 400', via a clearinghouse, for example, to request eligibility and benefit information related to the appointment that was set up. The HIPAA 270 transaction should include any scheduled services on the medical office's price list to be included in the appointment.

6) When process 410' of payment system 400' receives the HIPAA 270 transaction, process 410' processes the HIPAA 270 transaction as follows:

a. If the subscriber ID is not an email address, process 410' looks up the subscriber ID in database 478. If found then an appointment record is created for the patient in appointment list 480. The appointment record includes the service date found in the DTP element in either the 2000C or 2000D loop of the HIPAA 270 transaction. The time of the appointment is set to noon, or some other time based on default values established within payment system 400'. Services in the EQ elements are set up as scheduled services; if no services are provided, then the 99213 service (or equivalent on the medical office's price list) is scheduled. If the appointment scheduled services can be pre-authorized, at this point they are pre-authorized.

b. If the subscriber ID is an email address, then the appointment is treated as an unregistered patient appointment and a registration email is sent to the subscriber's email address to request that they register for the service prior to the appointment. If the subscriber does not register prior to the appointment the medical office staff will be required to enter the payment information upon check in.

7) Process 410' will construct a 271 response as follows:

a. If the subscriber existed, had a valid payment method, and a pre-authorization for the scheduled services was successful, then a response of Active Coverage is sent back in the EB01 element b. If the subscriber existed, had a valid payment method but the pre-authorization was pending due to the service date, then a response of Active—Pending Investigation is sent back in the EB01 element indicating that the office staff should check the pre-authorization nearer the appointment date on the payment system 400' site.

c. If the subscriber existed, but did not have a valid payment method for pre-authorization, then a response of Inactive—Pending Eligibility Update is sent back in the EB01 element d. If the subscriber does not exist, but a valid email address was provided to send registration information out, then a response of Inactive—Pending Investigation is sent back in the EB01 element 8) Process 410' sends HIPAA 271 transaction back to medical office 301 with the appropriate trace numbers for the medical office to process the response and determine the appropriate course of action. The medical office will be able to confirm that the appointment is set up within the payment system by logging into the site for payment system 400'.

Figure 36:
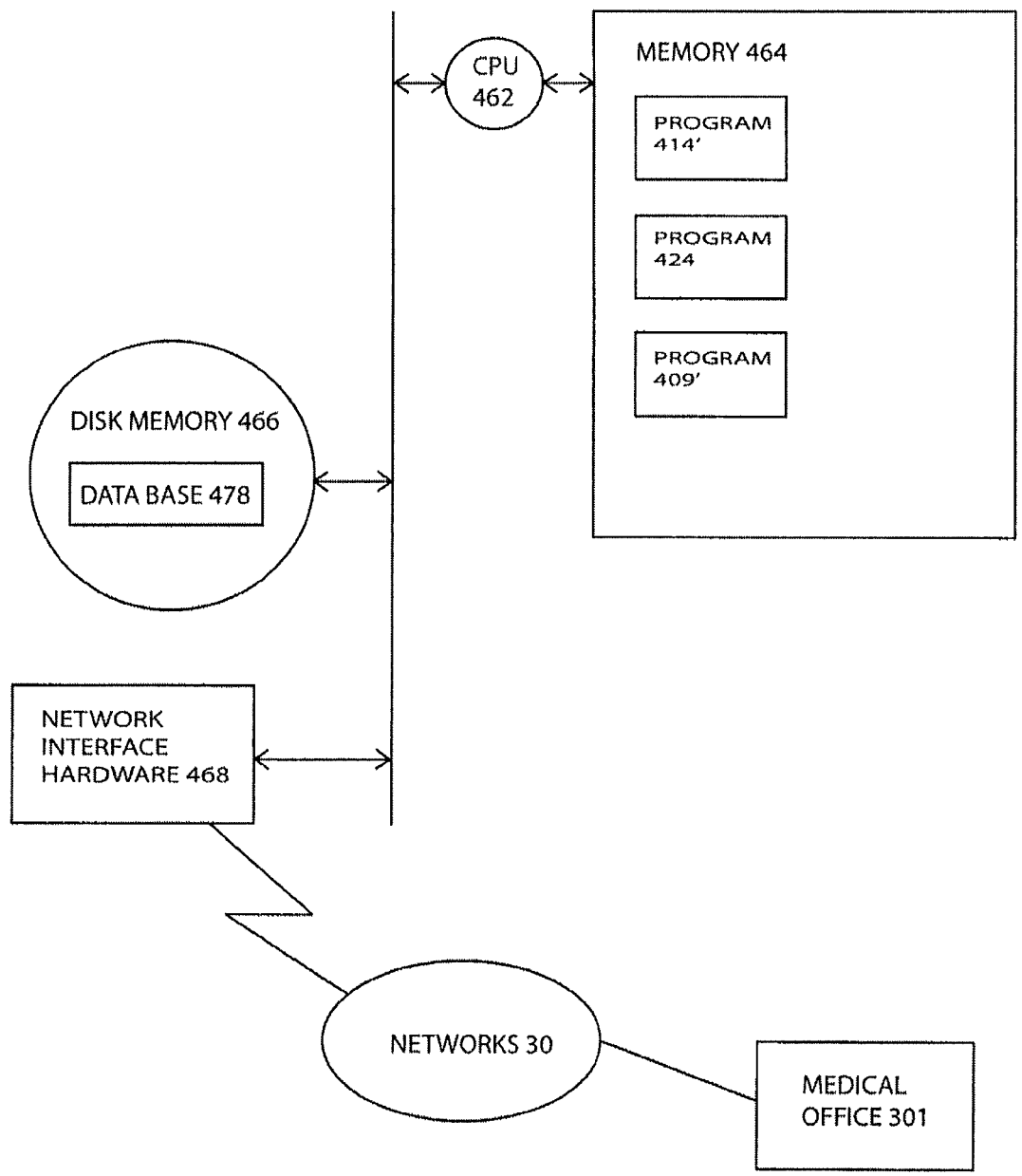
FIG. 36 is a diagram showing circuitry in a system.

FIG. 36 shows payment system 400' in more detail. CPU 462 executes program 414' (a plurality of computer instructions) to effect process 415' (FIG. 35). CPU 462 executes program 409' (a plurality of computer instructions) to effect process 410' (FIG. 35). CPU 462 executes program 424 (a plurality of computer instructions) to effect process 425 (FIG. 35).

In another scenario, a person 14 has accounts with credit card company 28, insurance company 21, insurance company 25, payment system 400', and medical office 301'.

Figure 37:
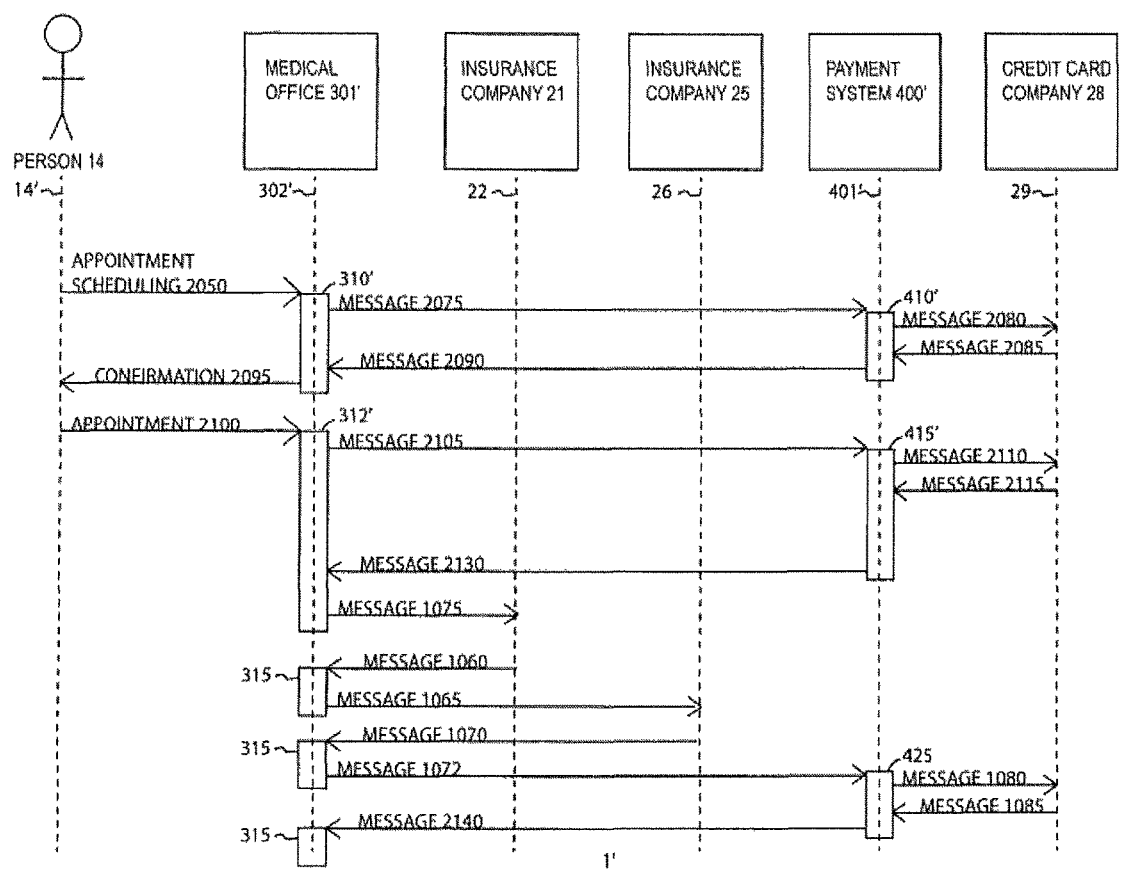
FIG. 37 shows a sequence of messages.

FIG. 37 shows a process wherein insured person 14 requests an appointment with medical office 301'. Responsive to the request from person 14, staff in medical office 301' invokes computer program 317 (FIG. 14) to send a message 2075 to payment system 400'. Payment system 400' processes message 2075, as described in connection with the scenario for person 12 above.

Person 14 visits medical office 301' for the scheduled appointment, and receives a medical service (appointment 2100).

Once the appointment is complete, staff of medical office 301' invokes a program to send a message to payment system 400' (message 2105). In response to receiving message 2105, payment system 400' may capture the amount pre-authorized in message 2080 from the credit card provided by the patient (messages 2110 and 2115).

Medical office 301' eventually sends a HIPAA 837 transaction (message 1075) to insurance company 21. Subsequently, after insurance company 21 determines the payment obligation of insurance company 21, insurance company 21 sends a HIPAA 835 transaction (message 1060) to medical office 301'.

Responsive to receiving message 1060, medical office 301' invokes computer process 315, which constructs and sends a HIPAA 837 transaction to insurance company 25 (message 1065) based on the received HIPAA 835 transaction (message 1060).

Subsequently, after insurance company 25 determines the payment obligation of insurance company 25, insurance company 25 sends a HIPAA 835 transaction (message 1070) to medical office 301'.

Responsive to receiving message 1070, medical office 301' invokes computer process 315, which constructs and sends a HIPAA 837 transaction to payment system 400' (message 1072) based on the received HIPAA 835 transaction (message 1070).

Responsive to receiving the HIPAA 837 transaction (message 1072), payment system 400' sends a charge request (message 1080) to credit card company 28, if necessary, after deducting the amount collected at time of service. Credit card company 28 determines whether to accept the charge and sends the result of the determination (message 1085) to payment system 400'.

Responsive to receiving message 1085, payment system 400' constructs and sends a HIPAA 835 transaction (message 2140) based on the message received from credit card company 28 (message 1085).

If payment system 400' has over collected from the patient at time of service, then any overpayments will be refunded and the paid to provider amounts adjusted as appropriate.

Figure 38:
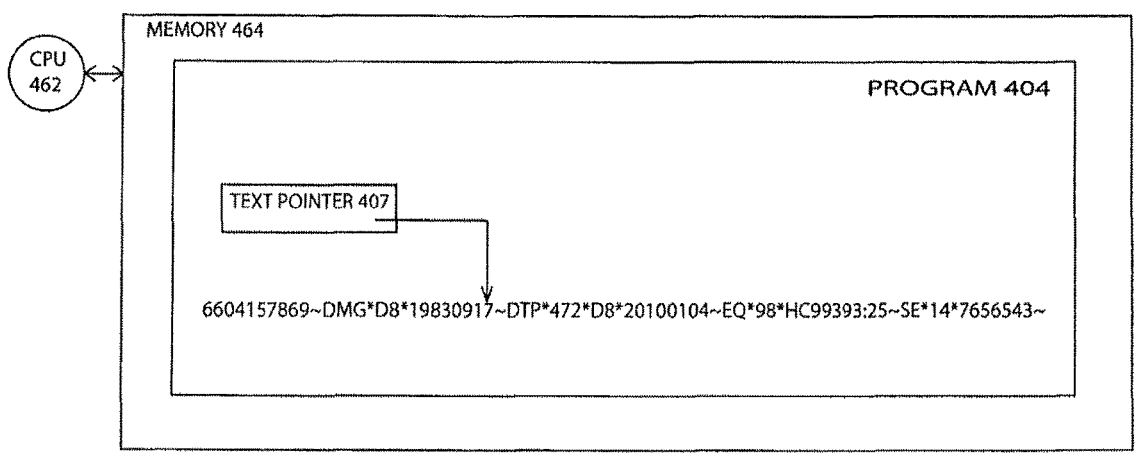
FIG. 38 is a diagram describing an aspect of a program at a certain time.

FIG. 38 is a diagram describing an aspect of program 404. Program 404 parses the HIPAA 270 transaction in message 3075 (FIG. 13) by recognizing certain tags and delimiters. Program 404 increments text pointer 407 as parsing progresses. At the time depicted in FIG. 38, program 404 is parsing the text of the date of birth element in the "DMG" segment.

Figure 39:
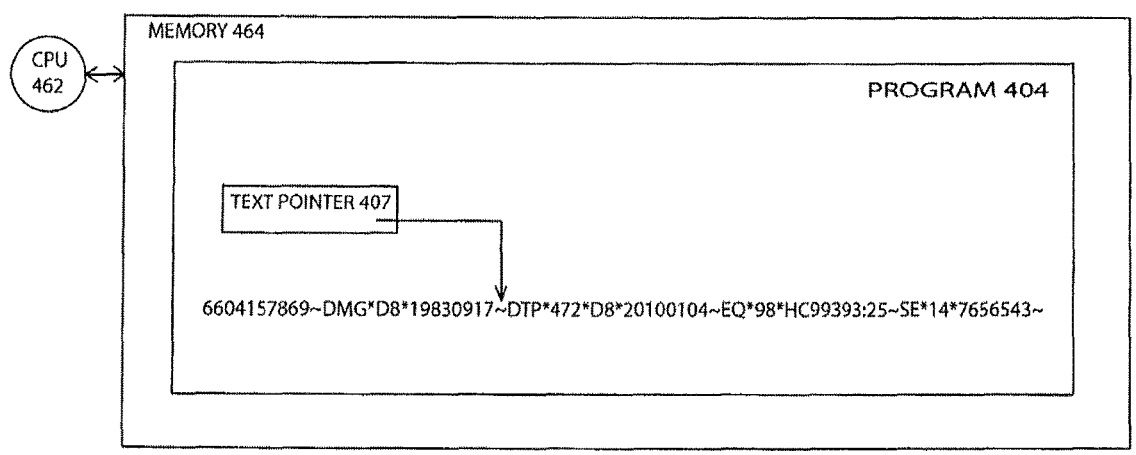
FIG. 39 is a diagram describing the aspect of the program at a subsequent time.

At the time depicted in FIG. 39, program 404 has recognized the character that delimits segments (".about.").

Figure 40:
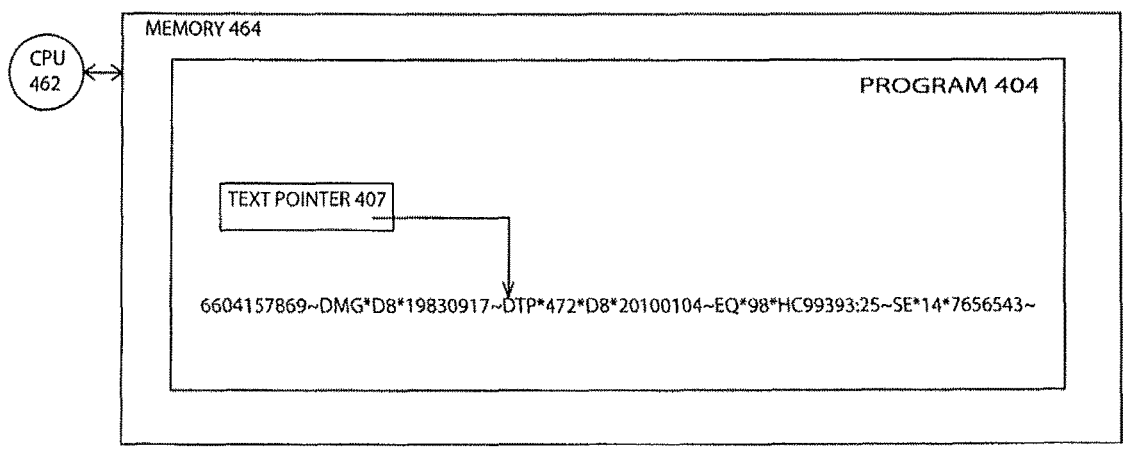
FIG. 40 is a diagram describing the aspect of the program at a subsequent time.

At the time depicted in FIG. 40, program 404 is in the process of recognizing tags a tag identifying a segment. At the time depicted in FIG. 40, the token candidate is "D".

Figure 41:
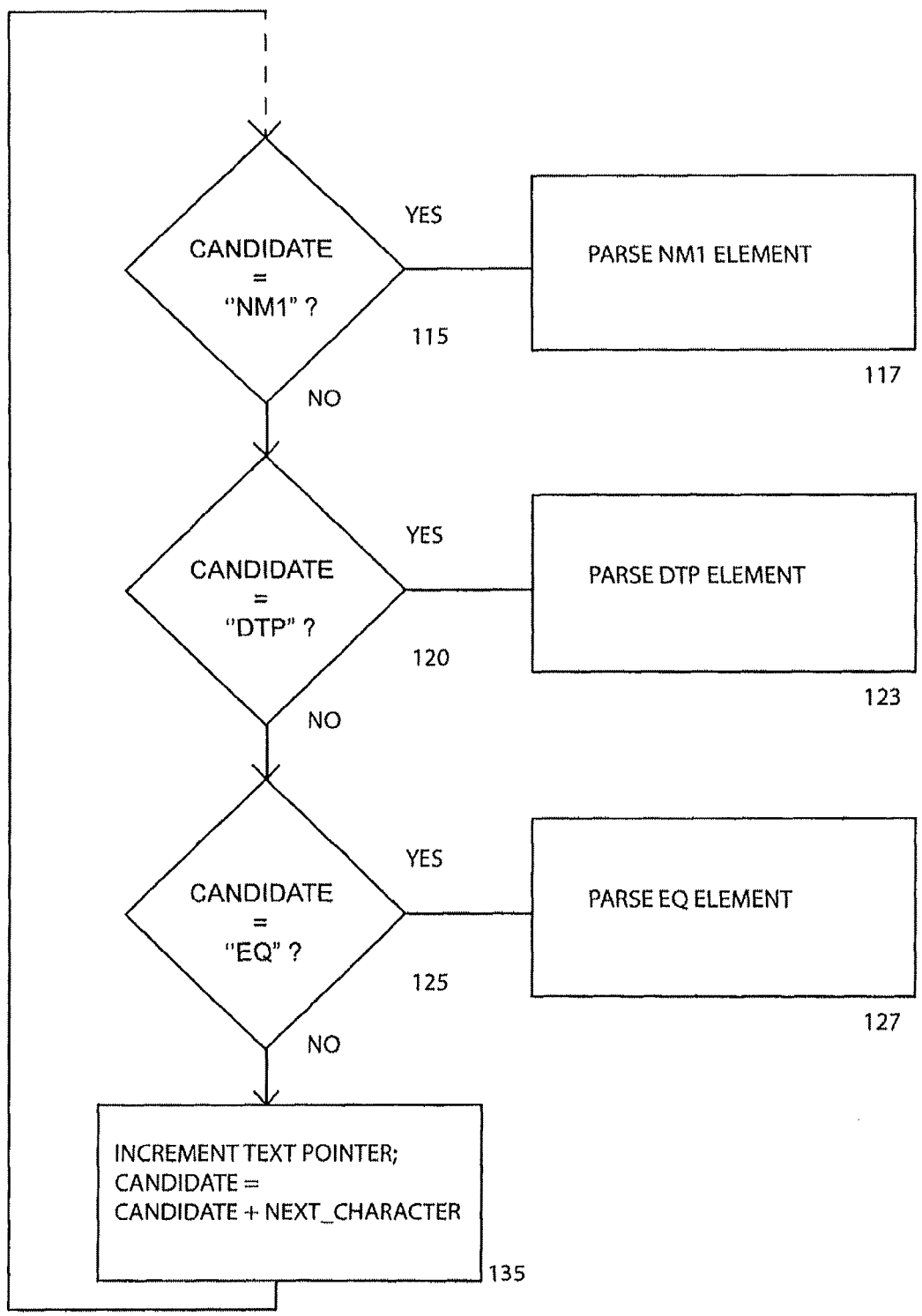
FIG. 41 is a flowchart describing a process shown in FIG. 13.

FIG. 41 is a flow chart describing another aspect of program 404,

Program 404 compares the current token candidate to "DTP" (step 120). If the current token candidate is not equal to "DTP", program 404 compares the current token candidate to "EQ" (step 125). Eventually, program 404 increments text pointer 407 so that text pointer 407 points to the next character in the HIPAA 270 transaction, and reads the next character, so that the current token candidate includes the next character (step 135).

Figure 42:
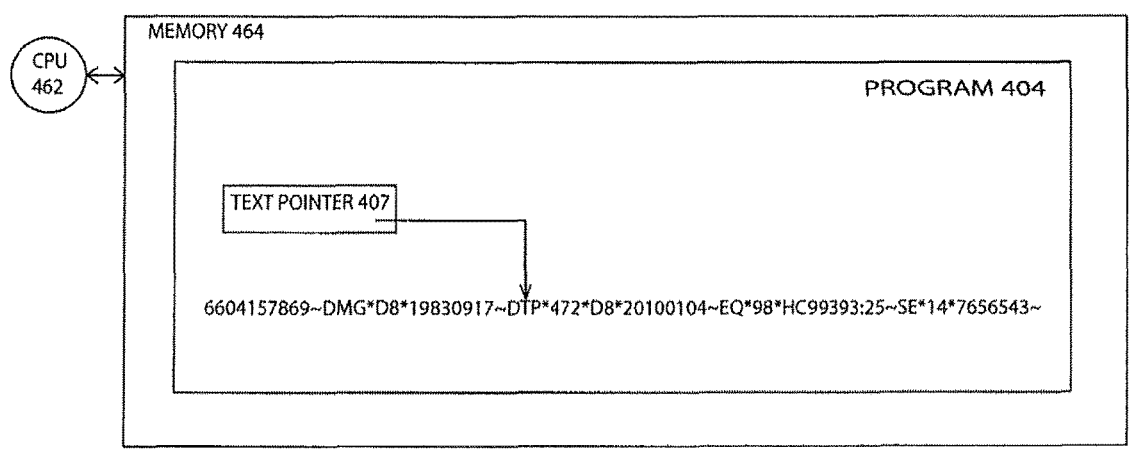
FIG. 42 is a diagram describing the aspect of the program at a subsequent time.

At the time depicted in FIG. 42, the token candidate is "DT".

Figure 43:
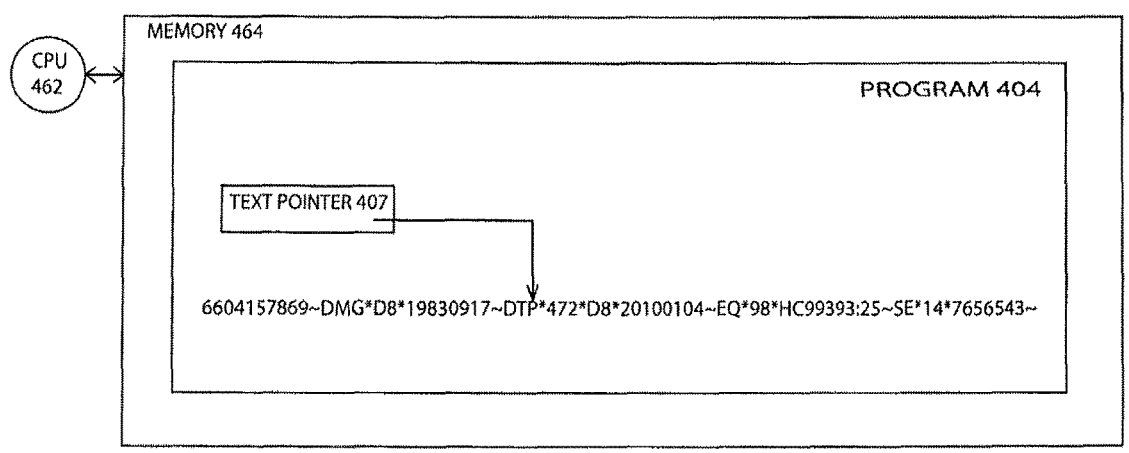
FIG. 43 is a diagram describing the aspect of the program at a subsequent time.

At the time depicted in FIG. 43, the token candidate is "DTP".

If step 120 detects the "DTP" tag, program 404 parses the following DTP segment (step 123).

Program 404 includes additional logic that recognizes tags and delimiters in addition to that represented by the boxes shown in FIG. 41. This additional logic is represented by the dashed line entering step 115.

Figure 44:
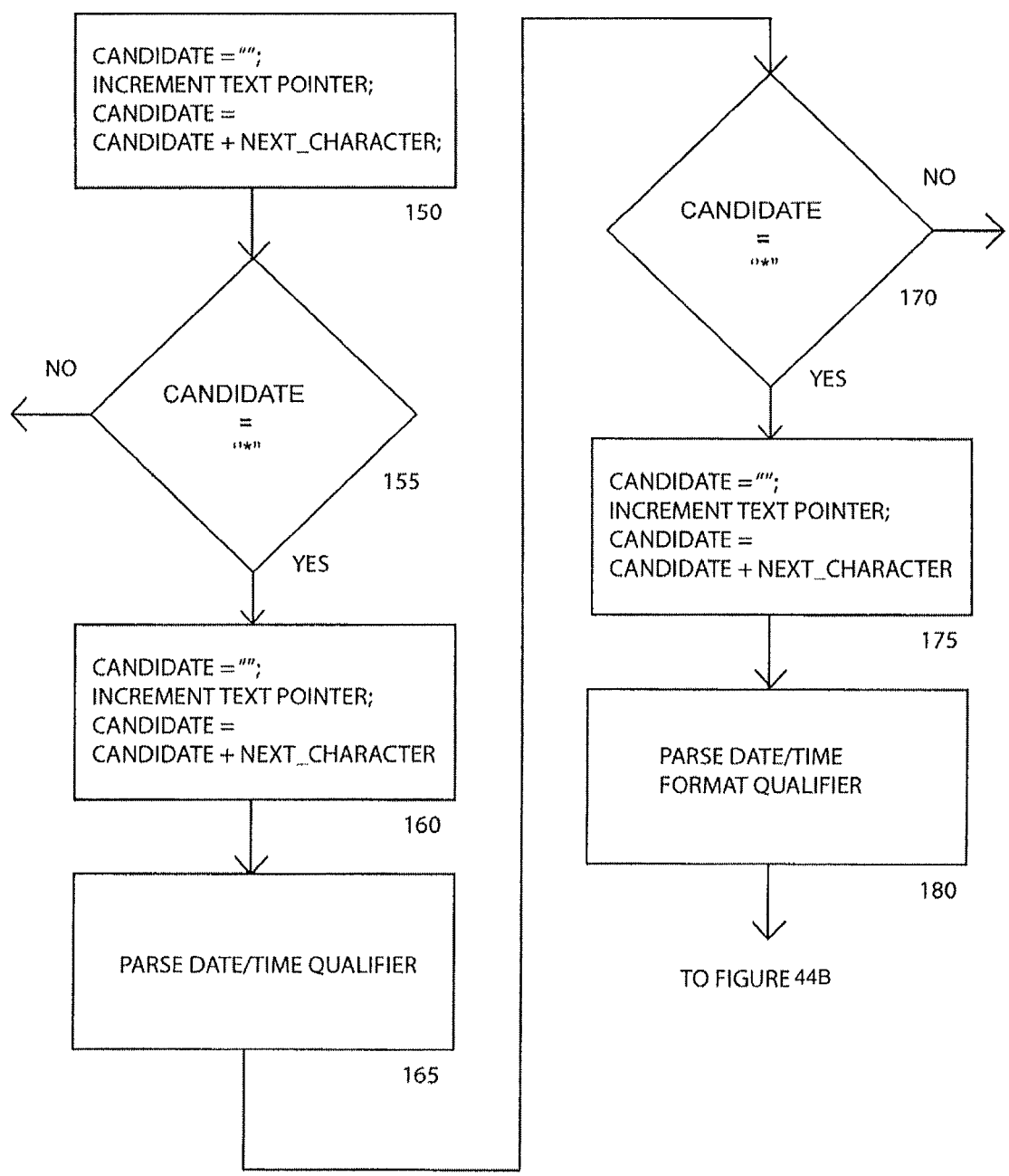
FIGS. 44A and 44B constitute a flow chart.
Figure 44:
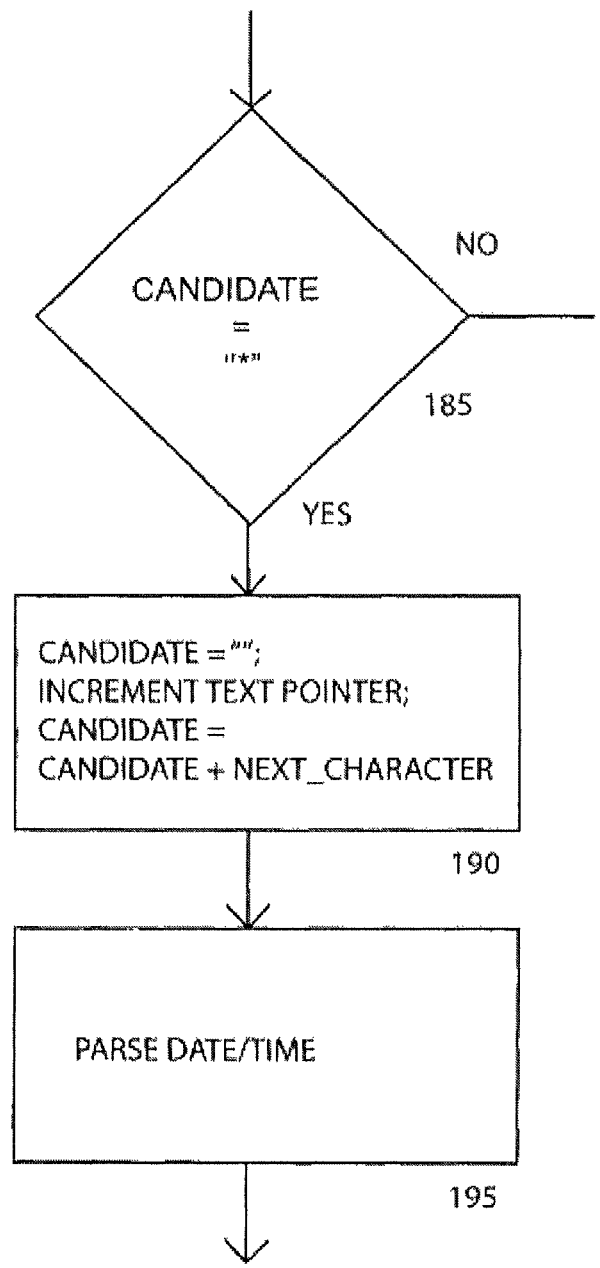

FIGS. 44A, 44B constitute a flow chart describing step 123 of FIG. 41 in more detail. Program 404 sets the token candidate to null and reads in the next character (step 150). If the token candidate is "*", program 404 sets the token candidate to null and reads the next character (step 160). If at step 155 the token candidate is not "*", error processing is performed, as represented by the NO exit path out of step 155 because, according to the HIPAA 270 transaction protocol, the next character should be "*".

There are numerous ways a person of skill in the art may implement the above-described parsing function of program 404. For example, the person could write a subprogram, using a higher level language for example, to carry out the parsing function of program 404. Alternatively, the person could invoke an off the shelf, commercially available tool, such as the Electronic Data Interchange (EDI) parser Trading Partner from Emanio Corporation, ProEDI, or Softshare. These products enable parsing of EDI transactions from trading partners and translating into other data structures such as database tables, flat files, XML files, etc. that are usually actionable by an application.

In particular Trading Partner can parse the transaction and then another Emanio product, called Unite!, can map the parsed data into database commands that load the data into a database. To generate the HIPAA 271 transaction, the software takes information in the database and translates the information into a HIPAA 271 transaction that is sent to the provider.

Figure 45:
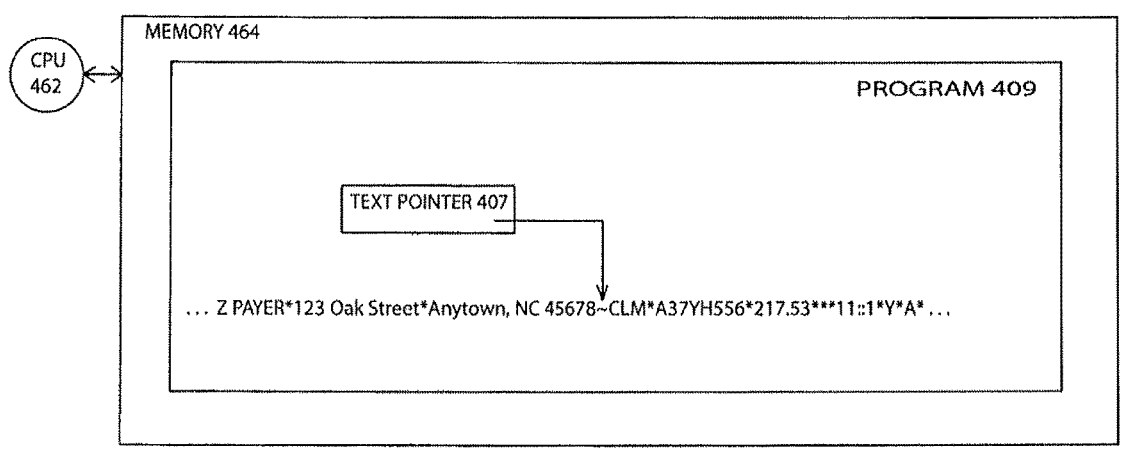
FIG. 45 is a diagram describing a parsing operation

FIG. 45 is a diagram describing an aspect of program 409. Program 409 parses the HIPAA 837 transaction in message 1075 (FIG. 13) by recognizing certain tags and delimiters. Program 409 increments text pointer 407 as parsing progresses. At the time depicted in FIG. 45, program 409 is parsing the text of an N4 element, containing postal address information for payment system 400.

At the time depicted in FIG. 45, program 409 has recognized the character that delimits segments (".about.").

Figure 46:
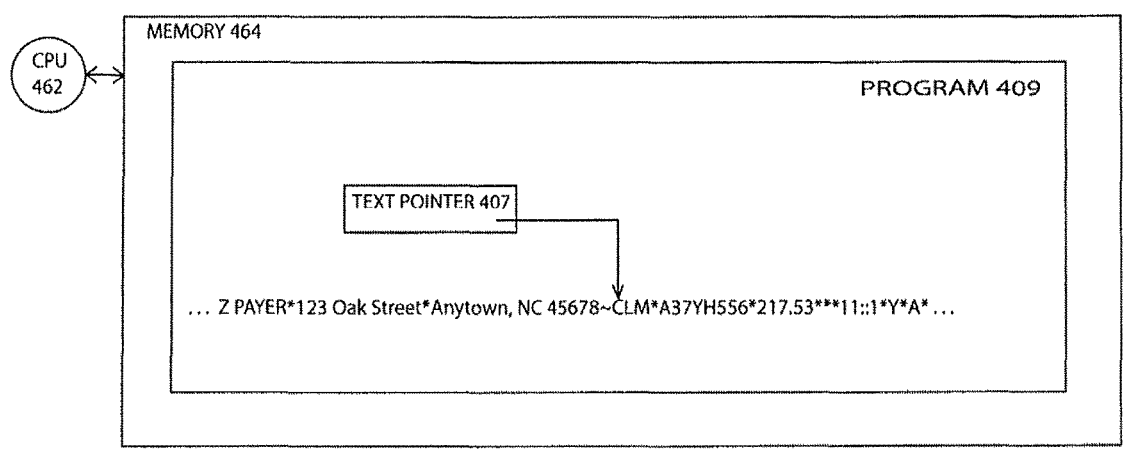
FIG. 46 is another diagram describing the parsing process.

At the time depicted in FIG. 46, program 409 is in the process of recognizing a tag identifying a segment. At the time depicted in FIG. 46, the token candidate is "C".

Figure 47:
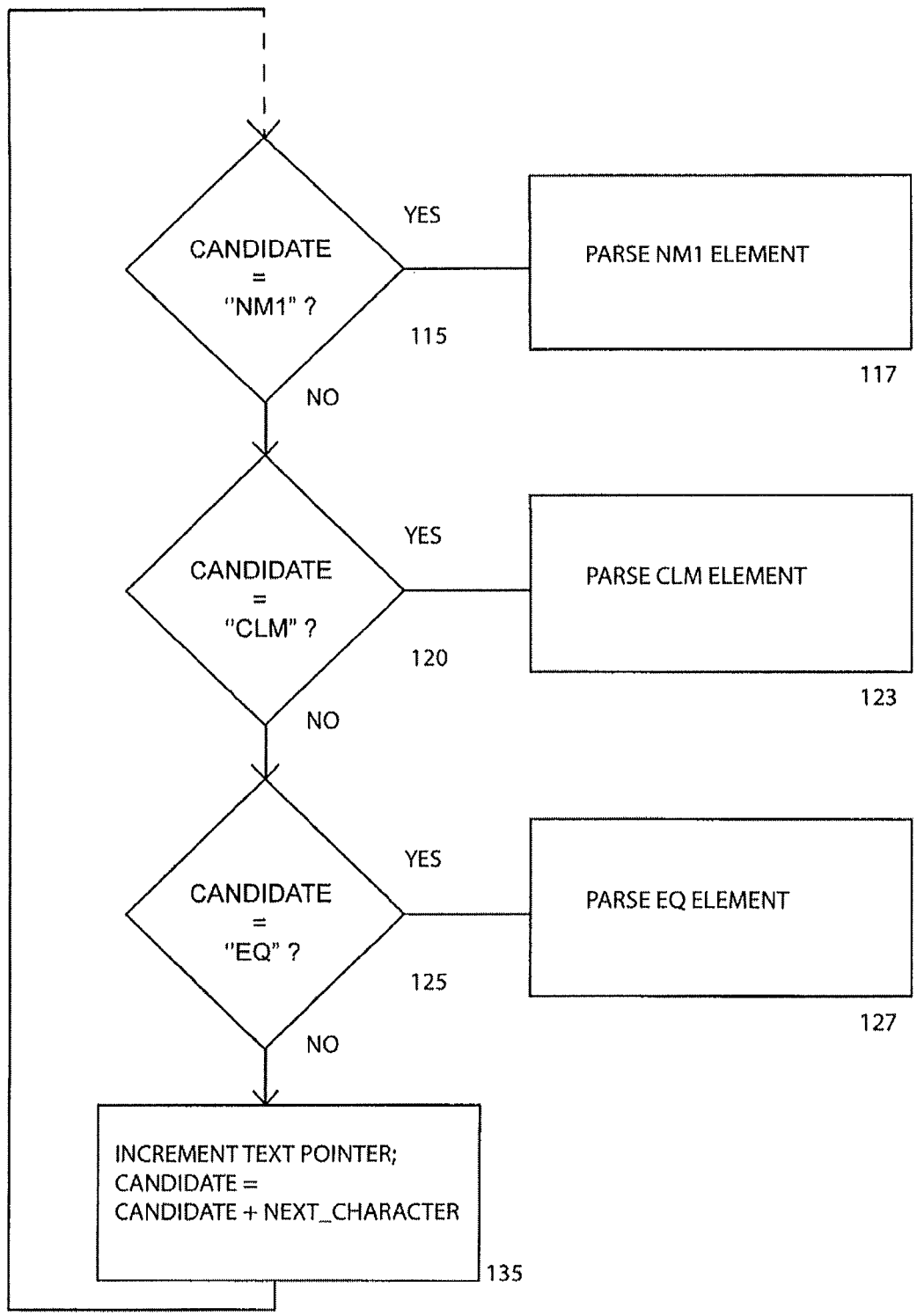
FIG. 47 is a flow chart describing the parsing process.

FIG. 47 is a flow chart describing another aspect of program 409.

Program 409 compares the current token candidate to "CLM" (step 120). If the current token candidate is not equal to "CLM", program 409 compares the current token candidate to "EQ" (step 125). Eventually, program 409 increments text pointer 407 so that text pointer 407 points to the next character in the HIPAA 837 transaction, and reads the next character, so that the current token candidate includes the next character (step 135).

Figure 48:
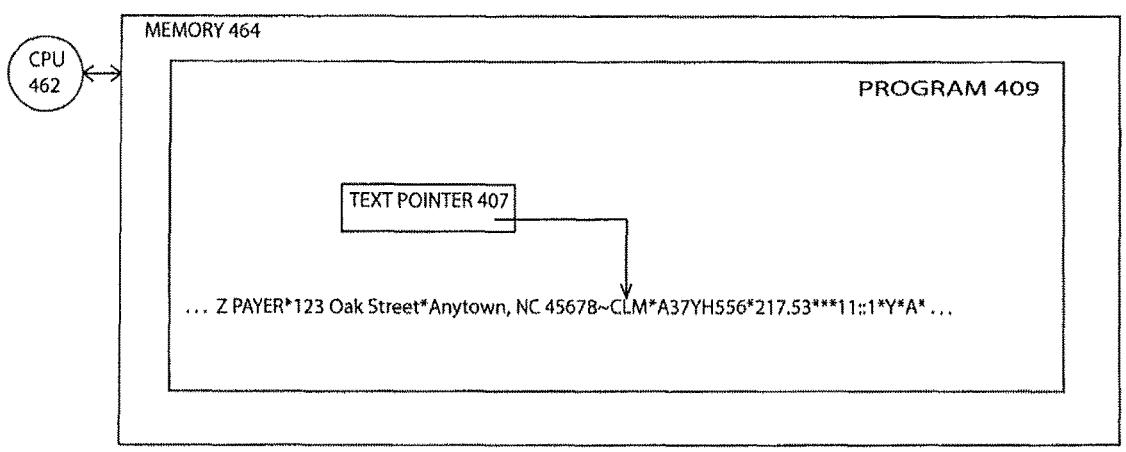
FIG. 48 is another diagram describing the parsing process.

At the time depicted in FIG. 48, the token candidate is "CL".

Figure 49:
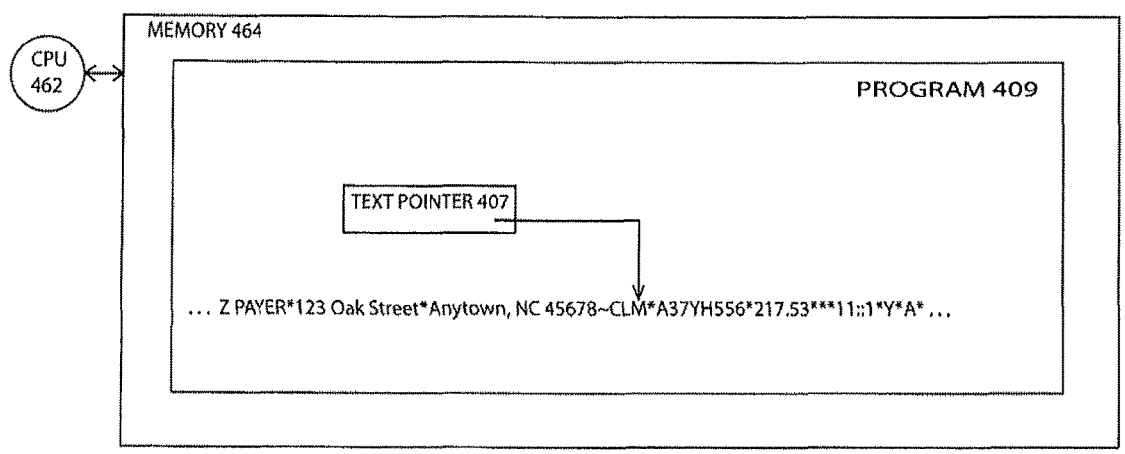
FIG. 49 is another diagram describing the parsing process.

At the time depicted in FIG. 49, the token candidate is "CLM".

If step 120 detects the "CLM" textual tag, program 409 parses the remainder of CLM segment (step 123), which has the format CLM*[Claim Submit Identifier (CLM01)]*[Monetary Amount (CLMO2)].

Figure 50:
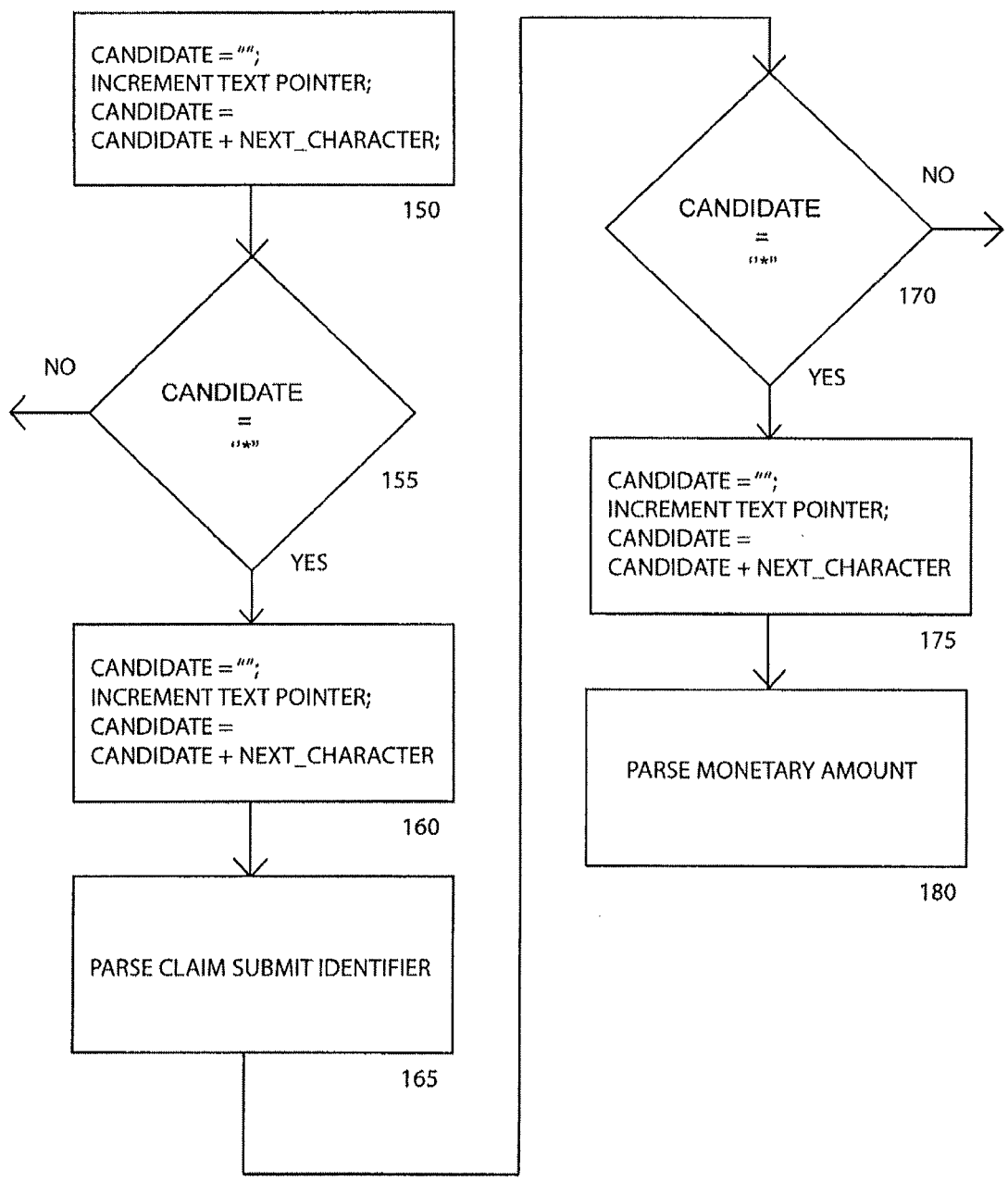
FIG. 50 is a flow chart describing a step of the parsing process in more detail.

Program 409 includes additional logic that recognizes tags and delimiters in addition to that represented by the boxes shown in FIG. 47, This additional logic is represented by the dashed line entering step 115, FIG. 50 is a flow chart describing step 123 of FIG. 47 in more detail. Program 409 sets the token candidate to null and reads in the next character (step 150). If the token candidate is "*", program 409 sets the token candidate to null and reads the next character (step 160). If at step 155 the token candidate is not "*", error processing is performed, as represented by the NO exit path out of step 155 because, according to the HIPAA 837 transaction protocol, the next character should be "*".

There are numerous ways a person of skill in the art may implement the above-described parsing function of program 409. For example, the person could write a subprogram, using a higher level language for example, to carry out the parsing function of program 409. Alternatively, the person could invoke an off the shelf, commercially available, tool, such as the Electronic Data Interchange (EDI) parser Trading Partner from Emanio Corporation, ProEDI, or Softshare. These products enable parsing of EDI transactions from trading partners and translating into other data structures such as database tables, flat files, XML files, etc. that are usually actionable by an application.

In particular Trading Partner can parse the transaction and then another Emanio product, called Unite!, can map the parsed data into database commands that load the data into a database. To generate the HIPAA 835 transaction, the software takes information in the database and translates the information into a HIPAA 835 transaction that is sent to the provider.

Figure 51:
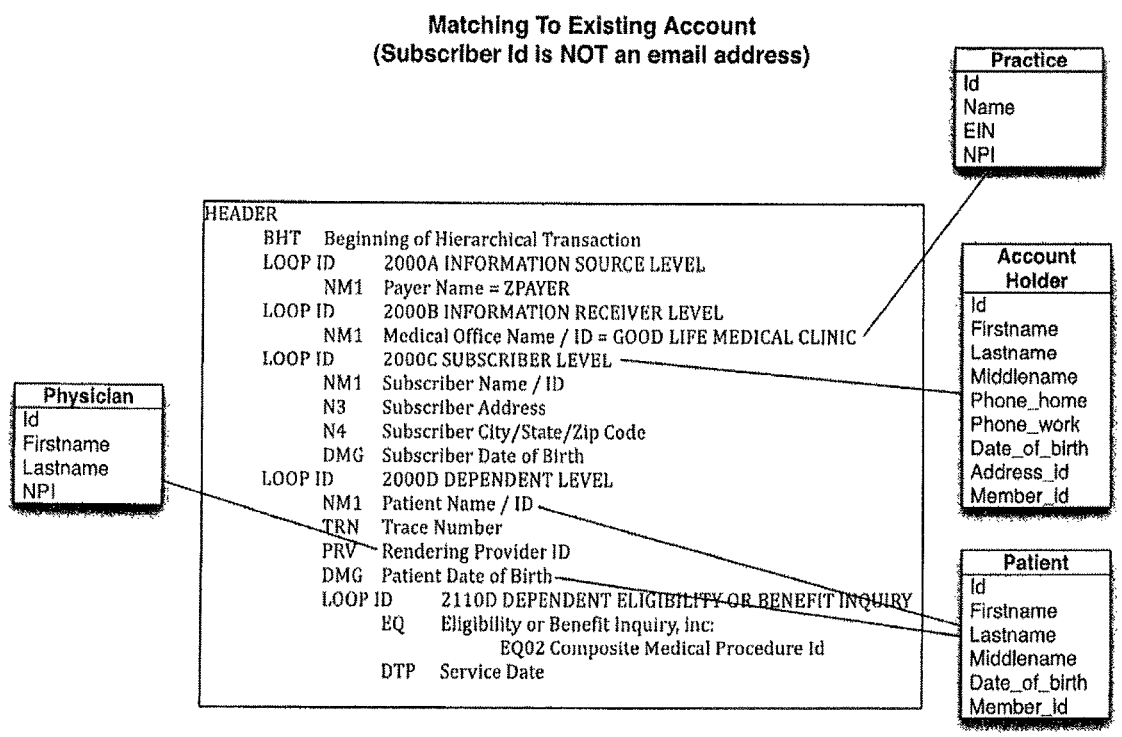
FIG. 51 is a diagram showing correspondence between a message and elements in a database.

FIG. 51 is a diagram for describing step 6a, in the text above, in more detail. The box "Account Holder" represents a list of records, each record storing data about a respective account holder. This list of records could be a list of JAVA objects (instances of an AccountHolder class). The first element ("Id") is an internal number unique to a particular AccountHolder Java object. The subsequent elements are data about a particular account holder.

The box "Practice" represents a list of records, each record storing data about a respective health care office. This list of records could be a list of JAVA objects (instances of a Practice class). The first element ("Id") is an internal number unique to a particular Practice Java object. The subsequent elements are data about a particular health care office.

The box "Physician" represents a list of records, each record storing data about a respective health care professional. This list of records could be a list of JAVA objects (instances of a Physician class). The first element ("Id") is an internal number unique to a particular Physician Java object. The subsequent elements are data about a professional.

The box "Patient" represents a list of records, each record storing data about a respective patient. This list of records could be a list of JAVA objects (instances of a Patient class), The first element ("Id") is an internal number unique to a particular Patient Java object. The subsequent elements are data about a particular patient.

A match of a HIPAA 270 transaction, to the information in database 478, requires that the first name, last name, and date of birth of the subscriber in the HIPAA 270 transaction matches either the member id or the first name, last name, and date of birth in one of the account holder records.

A match of the HIPAA 270 transaction, to the information in database 478, also requires that the practice ID in the HIPAA 270 transaction matches the practice NPI or EIN of one of the practice records.

A match of the HIPAA 270 transaction, to the information in database 478, also requires that the physician ID of the HIPAA 270 transaction matches a physician NPI of one of the physician records.

A match of the HIPAA 270 transaction, to the information in database 478, also requires that the first name, last name, and date of birth of the patient in HIPAA 270 transaction matches either the member id or the first name, last name, and date of birth of one of the patient records.

Figure 52:
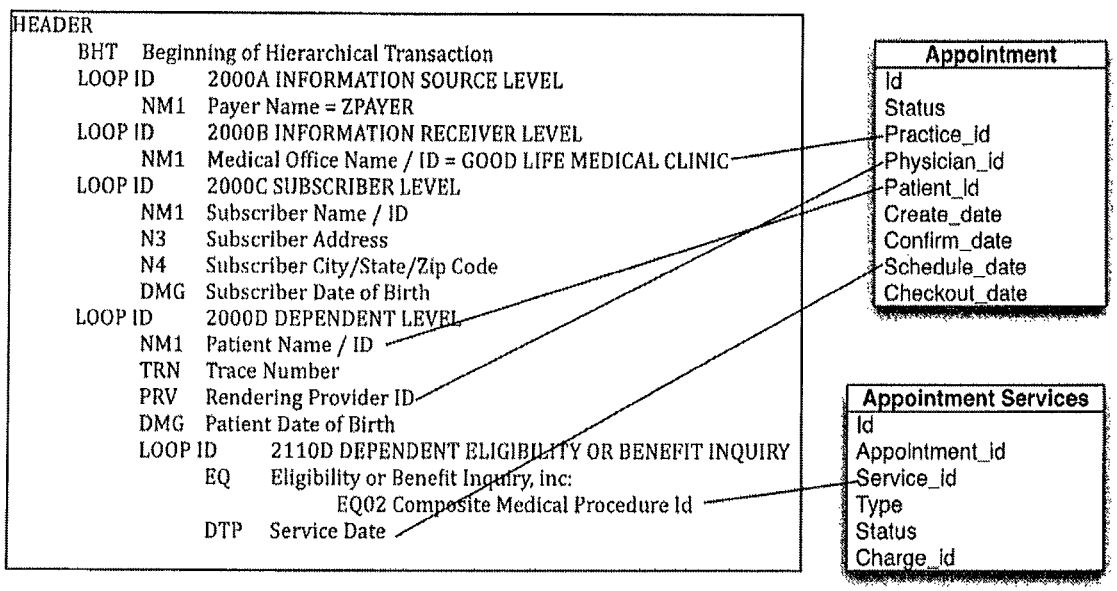
FIG. 52 is a diagram showing correspondence between the message and other elements in the database.

FIG. 52 is a diagram for describing the creation of an appointment record using the data in a HIPAA 270 transaction. The lines in FIG. 52 program 404 populates the appointment record elements depending on the contents of the HIPAA 270 transaction.

Each appointment record is linked to one or more "appointment services" record.

Figure 53:
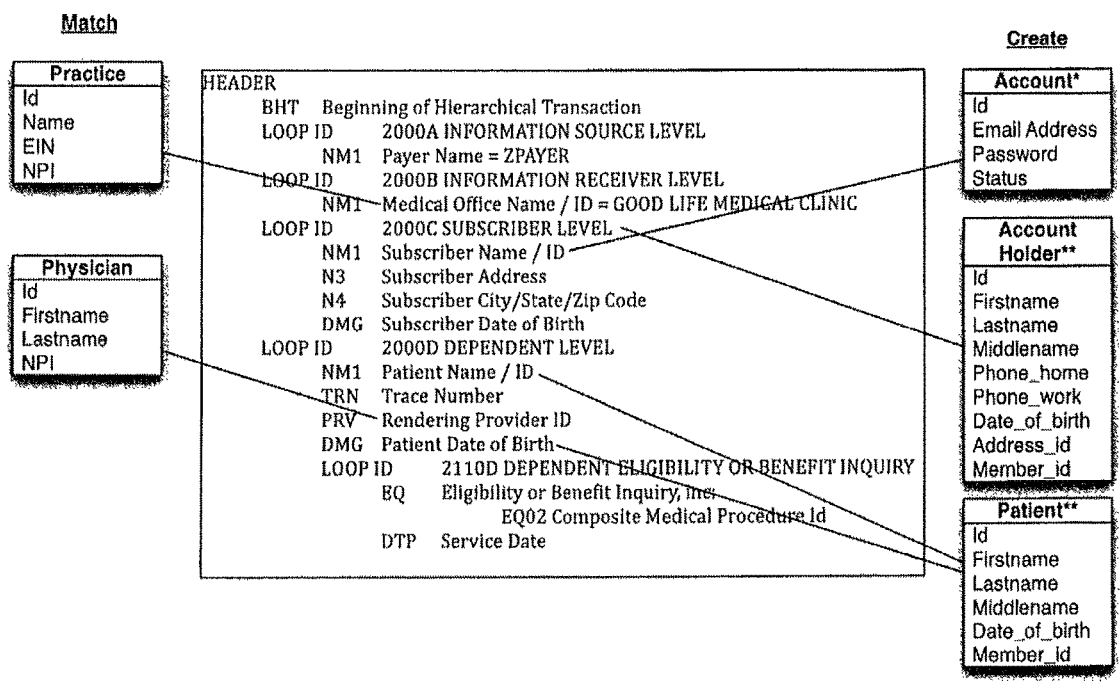
FIG. 53 is a diagram showing correspondence between the message and elements in the database.

FIG. 53 is a diagram for explaining step 6b, in the text above, in more detail. The lines in FIG. 53 show how program 404 populates various record elements depending on the contents of the HIPAA 270 transaction.

In another embodiment, competition may be generated at the medical service level. An insurer (i.e., an insurance company or an employer or government health plan) agrees to create a new insurance policy for its members, policy 10, and determines the premium for that policy based on standard actuarial methods. Instead of contracting with providers individually, the insurance plan simply determines the allowed amount they are willing to pay for each medical service and enter this into payment system 400". When a patient that has contracted for policy 10 is determining a provider to seek medical care from they would look up the provider in payment system 400". Payment system 400" would display the provider's cost for a service, and the insurance policy's allowed amount for the service, and therefore the amount that the patient responsibility would be (provider's stated charge minus the policy allowed amount). In some cases this amount may be significant, whereas for other providers the amount may be zero as the allowed amount covers the entire charge. This variation in patient responsibility will ensure that the patient tries to optimize what they consider cost effective, quality care to minimize their share of the cost. The provider will be forced to charge market rates in order to attract patients away from their competitors, and the insurance plan sponsors will be forced to optimize their allowed amounts for services to balance what a patient would pay in premiums versus out of pocket costs. Like existing products, the maximum out of pocket amount paid by the patient could be limited if necessary, although, given that the plan has less control over patient out of pocket costs it is likely that this deductible amount will have to be significantly high to deter patients from seeking more expensive care in order to get 'in benefits' quickly. The resulting set of market forces would control the cost of medical services as well as utilization of those services.

When the medical office sends the HIPAA 837 message to payment system 400", payment system 400" adjudicates the insured portion of the claim by comparing the charged amount to the allowed amount under the patient's policy, once determined though, payment system 400" will charge the patient's credit card for any positive difference between the charged amount and the allowed amount. As such, the single HIPAA 837 message is used to determine and pay both the insured portion and the patient responsibility portion and both payments will be detailed in the returned HIPAA 835 message.

In prior art insurance products, the allowed amount is negotiated individually with each provider, although the insurance company is likely to have a base allowed amount that they attempt to push onto smaller providers. This negotiated amount can be anything but is typically linked to the Medicare fee schedule, or some other published fee schedule, in order to create 'indexed' amounts that adjust annually without have to renegotiate the contract. In contrast, in payment system 400", the plan owners are provided the option of setting a single allowed amount for all providers, setting allowed amounts based on geographical location or linked to some other fee schedule such as Medicare, or going down to the individual provider level to set this pricing. The individual level is opens up a new source of competitive advantage for the plan owner in that they can increase the allowed amount for providers they consider to be high quality and cost effective and reduce the allowed amount for providers they consider to be low quality or not cost effective. By increasing the allowed amount the patient will experience less patient responsibility and therefore be 'steered' to the higher quality providers. This individual knowledge of the providers will become a competitive advantage for the plan owners in creating cost effective plan options.

In summary, in payment system 400", the provider sets their own fee schedule and the plan owner sets their own allowed amounts.

Payment system 400" presents the price as the provider's billed amount, then their insurance plan's allowed amount for the provider and service, and therefore the outstanding amount owed by the patient.

Payment system 400" collects both the insured portion and the patient portion of the payment based on a single HIPAA 837 claim and then applies both payments within the HIPAA 835 transaction.

In some embodiments, medical services may be paid for in installments. Payment system 400 may receive a claim (for example via an 837 transaction), from a medical office 301 for patient responsibility charges. Payment system 400 may process the claim received via the 837, as discussed above, and create a bill that is sent to the patient (e.g., person 12) electronically. Person 12 may be presented with a payment portal, allowing them to pay their bill, for example using a credit card or an ACH payment within a secure PCI Level 1 payment platform. Person 12 may have the option to pay for their charges using a payment plan, so they can pay their bill over a certain period of time set by the provider. Once the first payment has been captured towards the payment plan, a ASC X12 277 transaction can be sent electronically to the provider. In some embodiments, a partial ASC X12 835 transaction may be used in place of the 277 transaction. The 277 or 835 transaction can include information about the first payment so the partial record can be updated with the pertinent payment information so that the provider knows that the patient is in good standing based on their continued payments toward the payment plan. As the patient continues to pay towards the payment plan, subsequent 277 or 835 transactions may be sent after each payment is received. On the final payment, a ASC X12 835 (Payment/Advice) may be sent to the provider so the provider can automatically update the patient record with the pertinent payment information. The 835 transaction may indicate whether the patient has paid their bill in full or only partially. The provider may therefore know whether to shut down the process since the charges have been paid in full or create a paper statement for the patient.

Figure 54:
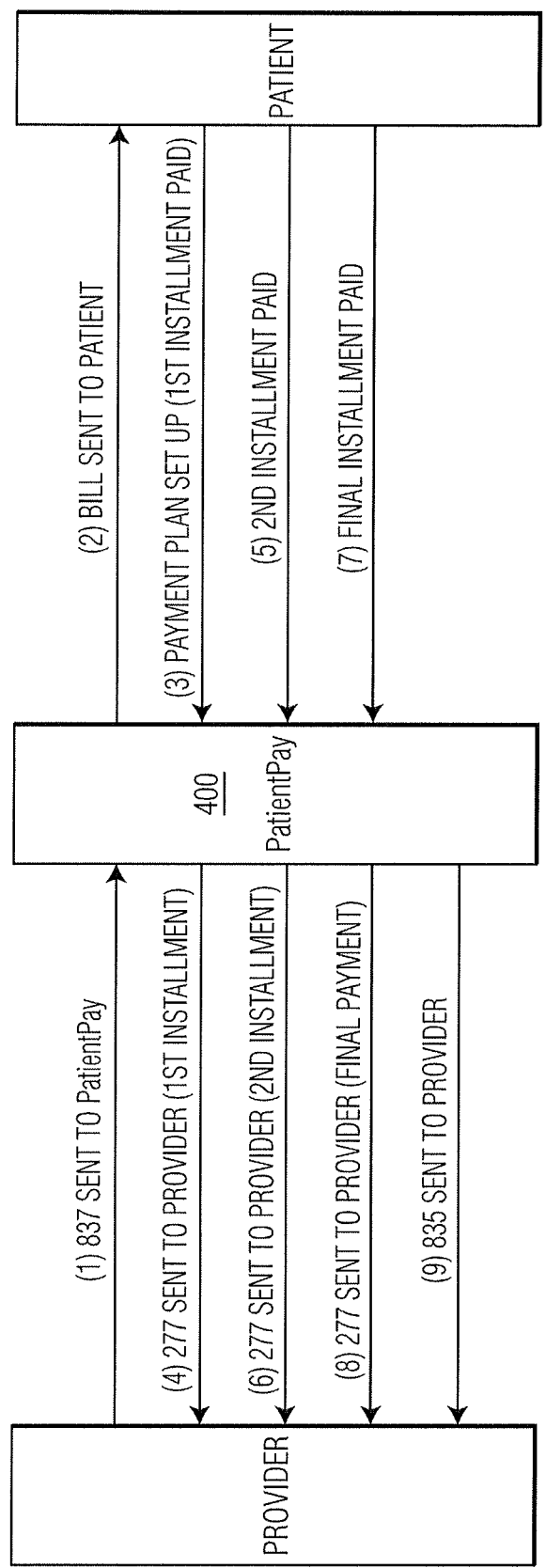
FIG. 54 shows a sequence of messages.
Figure 55:
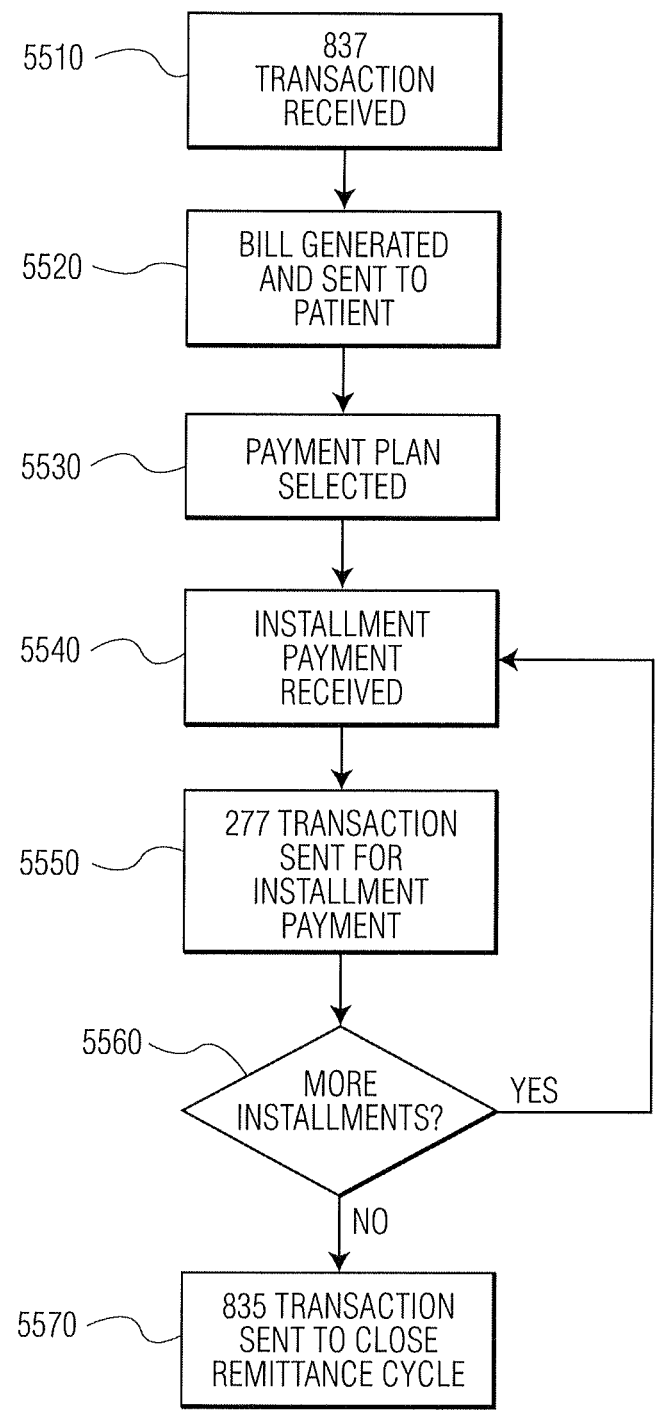
FIG. 55 is a flow chart describing an installment management process.

FIG. 54 shows a sequence of messages, and FIG. 55 is a flow chart describing an exemplary installment management process. According to an exemplary embodiment, the provider may send an 837 transaction (1) to payment system 400 At 5510, payment system 400 may receive the 837 transaction. The 837 transaction may include specific information about a patient's bill that is due based on services rendered by the provider. At 5520, a bill may be generated by payment system 400 with the details sent in the 837 transaction and sent (2) to the patient electronically.

At 5530, the patient may decide to use an optional payment plan to pay their bill/invoice. For example, the patient can elect to make three payments over three months, with one payment due per month (or any other number of payments over any number of pre-determined time periods). At 5540, the first installment may be collected (3) by payment system 400 from the patient's selected payment method (e.g., a credit card, check, etc.).

Once this payment is captured, at 5550 payment system 400 can generate a 277 transaction which is sent (4) to the provider. Note that while 277 transactions are used in the example of FIGS. 54 and 55, partial 835 transactions may also be used. The 277 transaction may include details about the payment made by the patient. The 277 transaction may include an STC segment in the 2200D loop to send claim level status information. Example code snippets for the STC segment may be as follows:

STC*P0:47*20130724**600*200****CHK1~
Or
STC*P0:72*20130724**600*200****CHK1~

In the examples, the claim status category code used in STC01-1=P0 and the claim status code used in STC01-2=47 or 72. STC02 depicts the date of payment, STC04 the total amount, STC05 the amount paid as the first installment of the payment plan, and STC09 the check number.

If more installments are pending in 5560, payment system 400 may repeat the process 5540-5550 for each installment. For example, in the three payment scenario, a second payment may be captured (5). Once the payment is secured, a 277 transaction may be sent (6) to the provider with details about this second payment. The 277 transaction may include an STC segment in the 2200D loop to send claim level status information. Example code snippets for the STC segment may be as follows:

STC*P0:47*20130824**600*200****CHK2~
Or
STC*P0:72*20130824**600*200****CHK2~

The second 277 transaction may be similar to the first except for a different date of payment and check number in STC02 and STC09 respectively.

In the three payment scenario, payment system 400 may collect the final installment (7) from the patient and a final 277 transaction may be sent (8) to the provider. The final 277 transaction may include details about the payment. The 277 transaction may include an STC segment in the 2200D loop to send claim level status information. Example code snippets for the STC segment may be as follows:

STC*P0:
47*20130924**600*200*20130924**20130930*CHK3~
Or
STC*P0:
72*20130924**600*200*20130924**20130930*CHK3~

The third 277 transaction may be similar to the others except for the following differences: STC02 may depict the date of final payment, STC06 may also depict the date of final payment (which is the final adjudication date), STC08 may depict the date the 835 payment advice will be sent to the provider, STC09 may depict the check number of the final payment sent to the provider when the 277 is issued.

In 5570, an 835 payment/advice transaction may be sent (9) to the provider to close the remittance cycle. If full payment has been received, the 835 transaction shows a $0 amount in the BPR segment with the service level loops indicating that all the amounts have been paid for the services. The amount depicted in the BPR segment is $0 because the prior 277 transactions have already reported the PAID charges along with the checks or etfs (or other forms of payment(s)) that have been sent to the provider. In the event there is still an amount due (e.g., the patient did not make all of the payments), the 835 may show an amount due within the service level loops indicating that there is still an amount owed by the patient for the services rendered.

Throughout this disclosure, certain processing may be depicted in real-time, batch, serial, parallel, or other fashion, for ease of description. Actual hardware and software realizations, however, may be varied depending on desired optimizations apparent to one of ordinary skill in the art.

The word circuitry encompasses dedicated database hardware, and/or programmable hardware, such as a central processing unit (CPU) or reconfigurable logic array, in combination with programming data, such as sequentially fetched CPU instructions or programming data for a reconfigurable array. Thus, circuitry encompasses, for example, a general-purpose electronic processor programmed with software, acting to carry out a described function.

Benefits, other advantages, and solutions to problems have been described above with regard to specific examples. The benefits, advantages, solutions to problems, and any element(s) that may cause any benefit, advantage, or solution to occur or become more pronounced are not critical, required, or essential features or elements of any of the claims.

Additional advantages and modifications will readily occur to those skilled in the art. The disclosure in its broader aspects is therefore not limited to the specific details, representative apparatus, and illustrative examples shown and described.

For example, although the examples show a person relying on a particular number of insurers, the number of insurers is variable. A person may rely on no insurers, one insurer, two insurers, etc.

For example, the person that pays for the health care services, or health care insurance, need not be the person that receives the health care services.

Although a payment mechanism has been described as being a credit card account, alternatives such as a debit card account, a gift card account, another type of account processed over a card-processing network, or other types of accounts may be employed.

For example, the order of messages and distribution of information among the messages may vary. Although message 1045, informing the medical office of the set of payers, has been depicted as sent before the visit for medical services, the subscriber could inform the medical office of a payer, or set of payers, during or after the visit to the medical office.

Instead of a subscriber informing the medical office of the complete set of payers in one message, such as message 1045, the subscriber may inform the medical office of a primary insurer on one day, and another entity payment on another day.

For example, although computer processing has been shown as being performed in the medical offices, a medical office could be equipped merely with a thin client and the bulk of the computer processing could be performed, under direction of the medical office, by another entity, geographically distant from the medical office, Although in the description provided above, the payment system and the insurance companies are non-affiliated, the payment system and the insurance companies could be affiliated.

Although, in the description provided above, message fields are located using textual tags within a message, fields could be located using an offset stored in a message, or using an offset stored external to the message.

Thus, departures may be made from such details without departing from the spirit or the scope of Applicants' general inventive concept. The invention is defined in the following claims. In general, the words "first," "second," etc., employed in the claims do not necessarily denote an order.

What is claimed is:

1. A system for efficient data processing comprising:
  a provider interface embodied in at least one computing device executing computer-readable instructions and in communication with one or more medical service entity devices, wherein the provider interface is unaffiliated with and communicates with the one or more medical service entity devices via standardized transactions, so that transactions from the one or more medical service entity devices to the provider interface are in a first format and transactions from the provider interface to the medical service entity devices are in a second format,
  wherein the data management system performs the following steps in order:
    1) the provider interface receives data relating to payment paid by one or more of insurance entities and patients for one or more medical services rendered by one or more medical service entities, the provider interface receiving the data directly from the one or more medical service entity devices in the first format,
    wherein the data management system is registered with the one or more medical service entity devices as a payer for one or more patients,
    2) in response to the data management system being registered with the one or more medical service entity devices as a payer for the one or more patients, the provider interface automatically receives the information and transmits the information to a processing engine, the processing engine embodied in at least one computing device executing computer-readable instructions,
    3) in response to the transmittal by the provider interface, said processing engine processes the received payment information and applies any payment information to any charges for the one or more medical services,
    4) the processing engine transforms the data relating to the payment information into an invoice based on the payment information and determines that the invoice is to be paid in a plurality of installments;
    5) in response to the determination by the processing engine, a payment interface embodied in at least one computing device executing computer-readable instructions requests payment of the invoice from one or more payment services, wherein said payment interface is in communication with the one or more payment services,
    6) the payment interface receives data relating to each of the plurality of installments from the one or more payment services and transmits the data relating to each of the plurality of installments to the provider interface,
    7) in response to the transmittal by the payment interface, the provider interface transforms the data relating to the plurality of installments into a transaction, in the second format, for each of the plurality of installments received by the payment interface comprising information about the installment and sends each of the transactions to the one or more medical service entity devices, and
    8) when transactions for each of the plurality of installments have been generated, the provider interface transmits information indicating completion of the plurality of installments to the one or more medical service entity devices in the second format.

2. The data management system of claim 1, wherein each transaction for each of the plurality of installments is a HIPAA 277 transaction or a partial HIPAA 835 transaction, the first format is a HIPAA 837 payment request transaction, and the second format is a HIPAA 835 payment confirmation transaction.

3. The data management system of claim 1, wherein each transaction for each of the plurality of installments comprises claim status information.

4. The data management system of claim 3, wherein the claim status information comprises claim category information, payment date information, payment amount information, total amount information, check information, or a combination thereof.

5. The data management system of claim 1, wherein one of the plurality of installments is a final installment, and wherein the transaction for the final installment comprises final payment information and a date at which the information indicating completion of the plurality of installments is to be sent.

6. The data management system of claim 1, wherein the information indicating completion of the plurality of installments comprises an indication that full payment for the one or more medical services has been received or an indication that payment for the one or more medical services is still owed.

7. The data management system of claim 1, wherein the format of communications between the one or more medical service entity devices and the provider interface is similar to the format of communications between the one or more medical service entity devices and one or more insurance entity devices, since the same format is used for transactions with the one or more medical service entity devices.

8. A method for efficient data processing, the method comprising the following ordered steps:
1) receiving, by a provider interface of a data management system, the provider interface embodied in a computing device executing computer-readable instructions, data relating to payment paid by one or more of insurance entities and patients for one or more medical services rendered by one or more medical service entities, the data received directly from one or more medical service entity devices in a first format, said provider interface being unaffiliated with said medical service entity devices,
   wherein the information relates to payment for one or more medical services rendered by one or more medical service entities and the information comprises payment from one or more of: insurance entities, patients, and payment entities,
   wherein the data management system is registered with the one or more medical service entity devices as a payer for one or more patients, and
   wherein the information is automatically received by the provider interface in response to the data management system being registered with the one or more medical service entity devices as a payer for the one or more patients;
2) transmitting, by the provider interface, the information to a processing engine of the data management system, the processing engine embodied in a computing device executing computer-readable instructions;
3) transforming, by the processing engine and in response to the transmitting by the provider interface, the data relating to the payment information into an invoice based on the information about the one or more medical services received by the provider interface;
4) determining, by the processing engine, that the invoice is to be paid in a plurality of installments;
5) in response to the determining by the processing engine, requesting, by a payment interface embodied in a computing device executing computer-readable instructions, payment of the plurality of installments from the one or more payment services;
6) receiving, by the payment interface, data relating to each of the plurality of installments from one or more payment services;
7) transmitting, by the payment interface, the data relating to each of the plurality of installments from one or more payment services to the provider interface;
8) transforming, by the provider interface in response to the transmittal by the payment interface, the data relating to the plurality of installments into a transaction in a second format for each of the plurality of installments received by the payment interface comprising information about the installment;
9) sending, by the provider interface, each of the transactions to the one or more medical service entity devices; and
10) when transactions for each of the plurality of installments have been generated, transmitting, by the provider interface, information indicating completion of the plurality of installments to the one or more medical service entity devices in the second format.

9. The method of claim 8, wherein each transaction for each of the plurality of installments is a HIPAA 277 transaction or a partial HIPAA 835 transaction, the first format is a HIPAA 837 payment request transaction, and the second format is a HIPAA 835 payment confirmation transaction.

10. The method of claim 8, wherein each transaction for each of the plurality of installments comprises claim status information.

11. The method of claim 10, wherein the claim status information comprises claim category information, payment date information, payment amount information, total amount information, check information, or a combination thereof.

12. The method of claim 8, wherein one of the plurality of installments is a final installment, and wherein the transaction for the final installment comprises final payment information and a date at which the information indicating completion of the plurality of installments is to be sent.

13. The method of claim 8, wherein the information indicating completion of the plurality of installments comprises an indication that full payment for the one or more medical services has been received or an indication that payment for the one or more medical services is still owed.

14. The method of claim 8, wherein the format of communications between the one or more medical service entity devices and the provider interface is similar to the format of communications between the one or more medical service entity devices and one or more insurance entity devices, since the same format is used for transactions with the one or more medical service entity devices.

* * * * *